US010845372B2

(12) United States Patent
Inagaki et al.

(10) Patent No.: US 10,845,372 B2
(45) Date of Patent: Nov. 24, 2020

(54) CANCER EVALUATION METHOD AND CANCER EVALUATION SYSTEM

(71) Applicant: Renatech Co., Ltd., Isehara (JP)

(72) Inventors: Seiichi Inagaki, Isehara (JP); Naoyuki Okamoto, Isehara (JP)

(73) Assignee: RENATECH CO., LTD., Isehara (JP)

( * ) Notice: Subject to any disclaimer, the term of this patent is extended or adjusted under 35 U.S.C. 154(b) by 39 days.

(21) Appl. No.: 15/511,329

(22) PCT Filed: Mar. 10, 2015

(86) PCT No.: PCT/JP2015/057005
§ 371 (c)(1),
(2) Date: Mar. 15, 2017

(87) PCT Pub. No.: WO2016/042805
PCT Pub. Date: Mar. 24, 2016

(65) Prior Publication Data
US 2017/0254821 A1 Sep. 7, 2017

(30) Foreign Application Priority Data

Sep. 15, 2014 (JP) .................... 2014-187170

(51) Int. Cl.
| *G01N 33/84* | (2006.01) |
|---|---|
| *G01N 33/574* | (2006.01) |
| *G16H 10/40* | (2018.01) |
| *G16H 50/30* | (2018.01) |

(52) U.S. Cl.
CPC .......... *G01N 33/84* (2013.01); *G01N 33/574* (2013.01); *G01N 33/57488* (2013.01)

(58) Field of Classification Search
CPC ....... G01N 2800/7028; G01N 2800/56; G01N 33/574; G01N 33/57488; G01N 33/84; G06K 9/00496
See application file for complete search history.

(56) References Cited

U.S. PATENT DOCUMENTS

| 2003/0203495 A1 | 10/2003 | Rupp |
| 2010/0017144 A1 | 1/2010 | Imaizumi et al. |

FOREIGN PATENT DOCUMENTS

| JP | 2005-524071 A | 8/2005 |
| JP | 2011-47715 A | 3/2011 |
| JP | 5470848 B2 | 4/2014 |
| WO | 03/091725 A1 | 11/2003 |

OTHER PUBLICATIONS

Gupta et al., Serum Trace Elements and Cu/Zn Ratio in Breast Cancer Patients, Journal of Surgical Oncology, vol. 16, No. 3, 1991, pp. 178-181 (4 pages), cited in the specification and ISR.
Pirinççi et al., Levels of Serum Trace Elements in Renal Cell Carcinoma Cases, Asian Pacific Journal of Cancer Prevention, vol. 14, 2013, pp. 499-502 (4 pages), cited in the specification.
Wu et al., Differentiation of Serum Levels of Trace Elements in Normal and Malignant Breast Patients, Biological Trace Element Research, vol. 113, 2006, pp. 9-18 (10 pages), cited in ISR.
Takagi, Discriminant analysis and multiple logistic model, Journal of Clinical and Experimental Medicine, vol. 174, No. 4, 1995, pp. 285-289 (5 pages, only in Japanese), cited in ISR.
Tan et al., Early prediction of lung cancer based on the combination of trace element analysis in urine and an Adaboost algorithm, Journal of Pharmaceutical and Biomedical Analysis, vol. 49, No. 3, 2009, pp. 746-752 (7 pages). cited in ISR.
International Search Report dated Jun. 16, 2015, issued in counterpart International application No. PCT/JP2015/057005 (2 pages).
Khanna, S.S. et al, "Circulating Immune Complexes and Trace Elements (Copper, Iron and Selenium) as Markers in Oral Precancer and Cancer: A Randomised, Controlled Clinical Trial", Head & Face, Medicine, Biomed Central, Oct. 16, 2006, vol. 2, No. 1, p. 33; cited in Extended (supplementary) European Search Report dated Sep. 25, 2017.
Leung, P.L. et al, "Pattern Recognition Analysis to the Variation of Nasal-Pharynx Cancer Patients' Trace Element Levels in Samples of Hair, Whole Blood, and Tissue", Biiological Trace Element Research, 1994, vol. 42, No. 1, pp. 1-7; cited in Extended (supplementary) European Search Report dated Sep. 25, 2017.
Kaba, M. et al, "Serum Levels of Trace Elements in Patients with Prostate Cancer", Asian Pacific Journal of Cancer Prevention, Mar. 30, 2014, vol. 15, No. 6, pp. 2625-2629; cited in Extended (supplementary) European Search Report dated Sep. 25, 2017.
Extended (supplementary) European Search Report dated Sep. 25, 2017, issued in counterpart European Application No. 15841232.0. (10 pages).

*Primary Examiner* — Christopher Adam Hixson
(74) *Attorney, Agent, or Firm* — Westerman, Hattori, Daniels & Adrian, LLP

(57) ABSTRACT

A cancer evaluation method includes a step S1 of measuring the concentrations of a set of evaluation elements in a serum sample 2 taken from a subject, a step S2 of applying the concentration data of the set of elements to a predetermined discriminant function to perform an operation; and a step S3 of discriminating whether or not the subject suffers from any type of cancer based on the operation result obtained using the concentration data and the discriminant function. The discrimination is carried out in accordance with the concentration balance (pattern) of the set of elements. Preferably, the set of elements are 7 elements of S, P, Mg, Zn, Cu, Ti, and Rb, or 16 elements of Na, Mg, Al, P, K, Ca, Ti, Mn, Fe, Zn, Cu, Se, Rb, Ag, Sn, and S.

12 Claims, 33 Drawing Sheets

FIG. 3

ESSENTIAL ELEMENTS LIST

| MAJOR ELEMENTS | TRACE ELEMENTS |
|---|---|
| hydrogen H | boron B |
| carbon C | fluorine F |
| nitrogen N | aluminium Al |
| oxygen O | silicon Si |
| sodium Na | vanadium V |
| magnesium Mg | chromium Cr |
| phosphorus P | manganese Mn |
| sulfur S | cobalt Co |
| chlorine Cl | nickel Ni |
| potassium K | copper Cu |
| calcium Ca | zinc Zn |
| iron Fe | arsenic As |
| | selenium Se |
| | molybdenum Mo |
| | iodine I |
| | bromine Br |

FIG. 4

| ELEMENT | BIOLOGICAL SIGNIFICANCE | RELATED MATTERS WITH CANCER |
|---|---|---|
| Na | important electrolyte; pH control of body fluid; osmotic pressure control in cells; transfers information by changing membrane potential of nerve cells; excessive intake causes hypertension | No Report |
| Mg | relates to enzymes for biosynthesis of proteins, nucleic acids, and lipids; distributed in bones, and muscles as phosphate and carbonate; deficiency causes muscle tremors and/or turbulence of pulse | in-serum concentration decreases with development of cancer |
| P | constituent element of nucleic acids (DNA, RNA); constitutes ATP and relates to energy metabolism; main component of teeth and bones | No Report |
| S | constitutes amino acides (methionine, cysteine, etc.); constitutes thiamine essential for growth; thiamine has anti-beriberi action and anti-neuritis action | No Report |
| K | important electrolyte; pH control of body fluid; metabolism promotion of cells; control of neural transmission function; functional control of muscles and heart | No Report |
| Ca | 90% exists in bones; activate various enzymes; relates to signal transmission among cells; deficiency causes rachitis, osteomalacia, and osteoporosis | No Report |
| Fe | essential for life; combined with proteins; hemoglobin in blood and myoglobin in muscles; conveys oxygen; deficiency causes anemia | in-serum concentration decreases with developmentof cancer |
| Cu | constitutes cytochrome c and caeruloplasmin; prevents arteriosclerosis and myocardial infarction; assists enzemes for maintaining normal strucure of blood vessels; excess causes acumulation in liver etc. resulting in hepatitis or liver cancer | in-serum concentration increases with developmentof cancer |
| Zn | relates to growth, gustation and olfaction; constitutes zinc finger proteins relating with cell generation and cytodifferentiation | in-serum concentration decreases with developmentof cancer |
| Se | cardiac insufficiency patient ofen have selenium deficiency; anti-inflammatory, immune enhancement, and metal detoxication action | in-serum concentration of cancer patients is lower than ordinary person |
| Rb | replaceable with potassium ions; deficiency causes decreased growth and ataxy | No Report |
| Ti | extremely small in living body; coexists with other elements (Pb, Al, Ba, Fe) | No Report |
| Ag | having sterilization action; significance in living body is unknown | new relationship is expected |
| Sn | physiological role in living body is unknown | new relationship is expected |

FIG. 5

| QUALITATIVE ANALYSIS RESULT | SAMPLE NAME | S1B | S3B | S6B | S8B | S9B | S10B | S11B | S12B | S13B | S14B |
|---|---|---|---|---|---|---|---|---|---|---|---|
| Na | ppb | 3160275.5 | 3213014.3 | 4689103.9 | 3170319.0 | 3180544.1 | 3289703.4 | 3227521.9 | 3251257.8 | 3234121.1 | 4525415.6 |
| Cl | ppb | 1368474.5 | 1595080.6 | 1628207.2 | 1284095.9 | 950244.1 | 1438225.2 | 1342256.8 | 1367756.5 | 1123481.6 | 2524278.5 |
| S | ppb | 1256663.7 | 1295221.2 | 1994250.5 | 1264261.4 | 1365403.1 | 1484463.4 | 1177543.9 | 1323441.2 | 1356605.8 | 1900193.0 |
| P | ppb | 247779.3 | 301612.9 | 329554.2 | 236640.7 | 221736.2 | 222647.1 | 228775.2 | 268165.5 | 230885.8 | 344754.4 |
| K | ppb | 148780.4 | 159583.3 | 211429.4 | 133070.1 | 145812.4 | 144222.0 | 139640.2 | 155968.0 | 152671.5 | 211359.1 |
| Ca | ppb | 69758.2 | 53599.9 | 89595.6 | 45667.3 | 54682.0 | 53846.6 | 51795.1 | 67363.2 | 65856.8 | 69225.5 |
| Mg | ppb | 20705.0 | 20453.9 | 28041.9 | 19136.4 | 20315.0 | 19562.5 | 21559.7 | 21795.2 | 20753.8 | 28925.8 |
| Br | ppb | 2155.8 | 18269.1 | 8598.9 | 3453.3 | 1787.3 | 2460.2 | 2201.4 | 2617.7 | 3019.8 | 119256.3 |
| Si | ppb | 6154.5 | 5787.6 | 11080.7 | 5693.3 | 7485.7 | 3501.5 | 27253.2 | 8875.2 | 3320.7 | 12132.1 |
| Fe | ppb | 1545.7 | 1385.9 | 2818.6 | 1267.7 | 1657.8 | 1587.7 | 994.4 | 1413.3 | 1890.8 | 3241.4 |
| Zn | ppb | 1284.5 | 830.4 | 1404.2 | 795.9 | 923.9 | 904.3 | 1141.2 | 1663.7 | 923.2 | 1588.1 |
| Cu | ppb | 965.6 | 714.0 | 1183.7 | 908.3 | 1115.7 | 742.7 | 1090.7 | 652.9 | 842.5 | 1407.5 |
| Ti | ppb | 366.6 | 306.3 | 1514.0 | 2551.0 | 1671.3 | 1283.5 | 565.8 | 295.9 | 1902.6 | |
| Pb | ppb | 125.1 | 166.3 | 245.1 | 116.6 | 149.3 | 133.1 | 115.7 | 180.0 | 148.5 | 209.7 |
| B | ppb | | 141.8 | | | | | | 144.2 | 148.1 | |
| Se | ppb | | 107.1 | | | | | 94.2 | 62.3 | | |
| Li | ppb | | 96.9 | | | 164.8 | 174.2 | | 131.5 | 101.2 | 236.4 |
| Al | ppb | 306.4 | 47.5 | 187.6 | 98.2 | 77.5 | | 29.2 | | 69.4 | |
| I | ppb | 39.7 | 43.9 | 125.2 | 45.0 | 37.1 | 31.6 | 58.9 | 55.7 | 30.4 | 73.3 |
| Sr | ppb | 42.2 | 22.4 | 30.4 | 36.7 | 20.4 | 21.7 | 46.5 | 35.8 | 25.7 | 18.8 |
| Ge | ppb | 16.9 | 12.6 | 26.7 | 29.8 | 22.1 | 24.2 | 7.4 | 12.8 | 7.5 | 43.9 |
| Ba | ppb | | 11.7 | | | | | | | | |
| Ni | ppb | 5.1 | 4.5 | 18.0 | 0.8 | 2.5 | 8.8 | 15.0 | 19.0 | 384.8 | 15.8 |
| As | ppb | | 4.3 | | | | | | 4.4 | | |
| Sb | ppb | | 2.4 | | 1.4 | 0.7 | 2.5 | 1.4 | | | |
| Mo | ppb | 1.4 | 1.7 | 24.7 | 2.7 | 3.5 | 4.0 | 6.2 | 2.6 | 9.1 | 16.9 |
| Hg | ppb | 2.2 | 1.4 | 1.2 | 2.7 | 1.5 | 0.7 | | 0.2 | 0.8 | 2.3 |
| Mn | ppb | | 1.4 | 1.7 | 0.4 | | 1.4 | 1.8 | 2.8 | 10.6 | 6.8 |
| Cs | ppb | 0.1 | 1.2 | 1.2 | 0.7 | 1.1 | 0.4 | 0.2 | 1.2 | 1.1 | 1.6 |
| Pt | ppb | 1.7 | 1.1 | | 0.5 | 1.1 | 2.4 | 1.7 | 1.8 | 0.6 | |
| Co | ppb | 0.7 | 0.2 | 0.5 | | 0.1 | 0.3 | | | 0.1 | 2.9 |
| W | ppb | | 0.2 | | | 0.0 | 0.4 | | | 0.3 | |
| Th | ppb | 1.5 | 0.2 | | 1.8 | | 0.3 | | | | 4.0 |
| Tl | ppb | | 0.1 | 0.1 | 0.2 | | | | | 0.4 | 0.2 |
| U | ppb | | 0.0 | | 0.1 | | | | 0.0 | | |

FIG. 6A (DOF: Degree of Freedom)

[TEST FOR POPULATION MEAN DIFFRENCE BETWEEN 2 GROUPS]
In Parentheses: Upper Row: DOF, Lower Row: Significance Probability
Group Variable: Subject (0: Control. 1: Case)

| Variable Name Group (Group Variable Value) | | | Sample No. | Mean | Unbiased Standard Deviation | Test for Equal Variance F-value | Test for Equal Variance t-valuez | Welch's Test t-value |
|---|---|---|---|---|---|---|---|---|
| N a       |           |         | 30 | 2925.312 | 529.655   | 28.423      | 2.518      | 3.058    |
| 1 ( 0.0 ~ | 0.0)      |         | 18 | 3108.021 | 617.663 ( | 17, 11) (   | 28 ) (     | 18.76)   |
| 2 ( 1.0 ~ | 1.0)      |         | 12 | 2651.250 | 115.855   | ( 0.0000)   | ( 0.0178)  | ( 0.0068)|
| C l       |           |         | 30 | 1532.867 | 304.694   | 2.635       | 0.049      | 0.053    |
| 1 ( 0.0 ~ | 0.0)      |         | 18 | 1535.111 | 356.568 ( | 17, 11) (   | 28 ) (     | 27.89)   |
| 2 ( 1.0 ~ | 1.0)      |         | 12 | 1529.500 | 219.648   | ( 0.1063)   | ( 0.9616)  | ( 0.9579)|
| S         |           |         | 30 | 1101.533 | 412.233   | 20.472      | 3.885      | 4.693    |
| 1 ( 0.0 ~ | 0.0)      |         | 18 | 1297.389 | 427.294 ( | 17, 11) (   | 28 ) (     | 19.42)   |
| 2 ( 1.0 ~ | 1.0)      |         | 12 | 807.750  | 94.437    | ( 0.0000)   | ( 0.0006)  | ( 0.0002)|
| P         |           |         | 30 | 251.467  | 85.761    | 1.911       | 0.603      | 0.565    |
| 1 ( 0.0 ~ | 0.0)      |         | 18 | 243.667  | 74.416 (  | 11, 17) (   | 28 ) (     | 18.55)   |
| 2 ( 1.0 ~ | 1.0)      |         | 12 | 263.167  | 102.873   | ( 0.2229)   | ( 0.5511)  | ( 0.5788)|
| K         |           |         | 30 | 142.633  | 21.426    | 5.524       | 2.602      | 3.004    |
| 1 ( 0.0 ~ | 0.0)      |         | 18 | 150.222  | 23.760 (  | 17, 11) (   | 28 ) (     | 24.67)   |
| 2 ( 1.0 ~ | 1.0)      |         | 12 | 131.250  | 10.110    | ( 0.0063)   | ( 0.0147)  | ( 0.0061)|
| C a       |           |         | 30 | 59.667   | 10.300    | 1.238       | 1.014      | 1.036    |
| 1 ( 0.0 ~ | 0.0)      |         | 18 | 61.222   | 10.708 (  | 17, 11) (   | 28 ) (     | 25.44)   |
| 2 ( 1.0 ~ | 1.0)      |         | 12 | 57.333   | 9.623     | ( 0.7335)   | ( 0.3195)  | ( 0.3101)|
| M g       |           |         | 30 | 18.633   | 3.528     | 6.637       | 3.407      | 3.972    |
| 1 ( 0.0 ~ | 0.0)      |         | 18 | 20.167   | 3.698 (   | 17, 11) (   | 28 ) (     | 23.68)   |
| 2 ( 1.0 ~ | 1.0)      |         | 12 | 16.333   | 1.435     | ( 0.0028)   | ( 0.0020)  | ( 0.0006)|
| B r       |           |         | 30 | 8.237    | 21.327    | 1784.614    | 1.029      | 1.268    |
| 1 ( 0.0 ~ | 0.0)      |         | 18 | 11.506   | 27.338 (  | 17, 11) (   | 28 ) (     | 17.03)   |
| 2 ( 1.0 ~ | 1.0)      |         | 12 | 3.333    | 0.647     | ( 0.0000)   | ( 0.3122)  | ( 0.2220)|
| F e       |           |         | 30 | 3.134    | 5.784     | 42.434      | 1.516      | 1.239    |
| 1 ( 0.0 ~ | 0.0)      |         | 18 | 1.856    | 1.361 (   | 11, 17) (   | 28 ) (     | 11.35)   |
| 2 ( 1.0 ~ | 1.0)      |         | 12 | 5.053    | 8.868     | ( 0.0000)   | ( 0.1407)  | ( 0.2411)|

FIG. 6B

| | | | | | | | | |
|---|---|---|---|---|---|---|---|---|
| Zn | | | 30 | 1.057 | 0.271 | 1.819 | 1.671 | 1.774 |
| 1 ( | 0.0 ~ | 0.0) | 18 | 1.122 | 0.290 | ( 17, 11) | ( 28 ) | ( 27.60) |
| 2 ( | 1.0 ~ | 1.0) | 12 | 0.958 | 0.215 | ( 0.3150) | ( 0.1060) | ( 0.0873) |
| Cu | | | 30 | 0.953 | 0.236 | 1.887 | 0.405 | 0.380 |
| 1 ( | 0.0 ~ | 0.0) | 18 | 0.939 | 0.206 | ( 11, 17) | ( 28 ) | ( 18.64) |
| 2 ( | 1.0 ~ | 1.0) | 12 | 0.975 | 0.283 | ( 0.2319) | ( 0.6888) | ( 0.7087) |
| Ti | | | 30 | 0.696 | 0.669 | 3.079 | 1.508 | 1.676 |
| 1 ( | 0.0 ~ | 0.0) | 18 | 0.843 | 0.764 | ( 17, 11) | ( 28 ) | ( 27.51) |
| 2 ( | 1.0 ~ | 1.0) | 12 | 0.475 | 0.435 | ( 0.0627) | ( 0.1428) | ( 0.1053) |
| Rb | | | 30 | 0.160 | 0.047 | 1.601 | 1.845 | 1.759 |
| 1 ( | 0.0 ~ | 0.0) | 18 | 0.173 | 0.041 | ( 11, 17) | ( 28 ) | ( 19.84) |
| 2 ( | 1.0 ~ | 1.0) | 12 | 0.142 | 0.051 | ( 0.3713) | ( 0.0757) | ( 0.0948) |

FIG. 7A

[DISCRIMINANT ANALYSIS]
CRITERION VARIABLE NAME: (1)SUBJECT

| GROUP | CRITERION VARIABLE VALUE/RANGE |
|---|---|
| 1 | 0.00 |
| 2 | 1.00 |

TABLE 1: CORRELATION COEFFICIENT MATRIX AMONG VARIABLES
[OVERALL]

| VARIABLE NAME | 1) | 2) | 3) | 4) | 5) | 6) | 7) |
|---|---|---|---|---|---|---|---|
| 1) S  | 1.000 | 0.097 | 0.712 | 0.206 | 0.234 | 0.128 | 0.347 |
| 2) P  | 0.097 | 1.000 | 0.325 | 0.089 | 0.185 | -0.094 | 0.308 |
| 3) Mg | 0.712 | 0.325 | 1.000 | 0.376 | 0.231 | 0.121 | 0.360 |
| 4) Zn | 0.206 | 0.089 | 0.376 | 1.000 | 0.264 | -0.081 | 0.187 |
| 5) Cu | 0.234 | 0.185 | 0.231 | 0.264 | 1.000 | -0.035 | 0.247 |
| 6) Ti | 0.128 | -0.094 | 0.121 | -0.081 | -0.035 | 1.000 | 0.036 |
| 7) Rb | 0.347 | 0.308 | 0.360 | 0.187 | 0.247 | 0.036 | 1.000 |

TABLE 2: 2-GROUP DISCRIMINATION:
LINEAR DISCRIMINANT COEFFICIENT

| VARIABLE NAME | DEISCRIMINANT COEFFICIENT |
|---|---|
| 1) S  | 0.004019 |
| 2) P  | -0.013291 |
| 3) Mg | 0.333628 |
| 4) Zn | 3.363696 |
| 5) Cu | -5.308847 |
| 6) Ti | 1.183276 |
| 7) Rb | 20.703250 |
| CONSTANT | -9.936799 |

| | |
|---|---|
| Mahalanobis' Dis. | 5.328012 |
| Misclass. rate | 12.422 % |
| F-VALUE | 4.306 |
| (DOF.1, DOF.2) | ( 7, 22) |
| p-VALUE | 0.003888 |

- Mahalanobis'Dis.:Mahalanobis' generalize Distance
- Misclass.rate: Misclassification Rate (Estimate Value)
- DOF: Degree of Freedom

TABLE 3: BOX'S M TEST

| | |
|---|---|
| $\chi^2$-VALUE | 51.270 |
| (DOF) | ( 28) |
| p-VALUE | 0.004651 |

FIG. 7B

TABLE 4: SIGNIFICANCE OF VARIABLES USED IN DISCRIMINANT ANALYSIS

| VARIABLE | WILK'S $\Lambda$ | INCREMENT OF $\Lambda$ | F-VALUE (DOF1, DOF2) | p-VALUE |
|---|---|---|---|---|
| 1) S  | 0.479362 | 0.057432 | 2.995 ( 1, 22) | 0.097549 |
| 2) P  | 0.469399 | 0.047468 | 2.475 ( 1, 22) | 0.129937 |
| 3) Mg | 0.446403 | 0.024473 | 1.276 ( 1, 22) | 0.270804 |
| 4) Zn | 0.453106 | 0.031176 | 1.626 ( 1, 22) | 0.215618 |
| 5) Cu | 0.485918 | 0.063988 | 3.336 ( 1, 22) | 0.081364 |
| 6) Ti | 0.449938 | 0.028008 | 1.460 ( 1, 22) | 0.239699 |
| 7) Rb | 0.457081 | 0.035151 | 1.833 ( 1, 22) | 0.189540 |
| OVERALL | 0.421930 | | | |

(WILKS' $\Lambda$ AND ITS VARIATION ARE SHOWN, WHEREIN EACH VARIABLE IS EXCLUDED.)

TABLE 5: SPURIOUS PERCENTAGE OF CORRECT CLASSIFICATIONS
(VERTICAL.: ACTUAL GROUP, HORIZONTAL.: GROUP BY DISCRIMINANT FUNCTION)

| GROUP | 1) | 2) | TOTAL |
|---|---|---|---|
| 1) | 16 | 2 | 18 |
| 2) | 1 | 11 | 12 |

PERCENTAGE OF CORRECT CLASSIFICATIONS: 86.667%

TABLE 6: BARYCENTER OF EACH GROUP IN DISCRIMINANT SPACE

| GROUP | 1ST AXIS |
|---|---|
| 1) | 2.131205 |
| 2) | -3.196807 |

FIG. 8

| No. | SUBJECT | Na | Cl | S | P | K | Ca | Mg | Br | Fe | Zn | Cu | Ti | Rb |
|---|---|---|---|---|---|---|---|---|---|---|---|---|---|---|
| 1 | CANCER | 2,958 | 1,737 | 893 | 510 | 138 | 64 | 18 | 3.6 | 19.0 | 0.9 | 1.0 | 0.7 | 0.20 |
| 2 | CANCER | 2,753 | 1,752 | 863 | 242 | 127 | 60 | 19 | 4.5 | 1.8 | 0.8 | 0.8 | 0.2 | 0.10 |
| 3 | CANCER | 2,682 | 1,572 | 850 | 441 | 137 | 48 | 17 | 3.9 | 1.0 | 0.9 | 1.0 | 0.5 | 0.20 |
| 4 | CANCER | 2,638 | 1,645 | 973 | 255 | 117 | 72 | 16 | 3.2 | 0.5 | 0.7 | 1.2 | 0.2 | 0.10 |
| 5 | CANCER | 2,649 | 1,536 | 876 | 247 | 131 | 53 | 17 | 3.6 | 1.1 | 0.9 | 0.9 | 0.1 | 0.10 |
| 6 | CANCER | 2,586 | 1,527 | 760 | 219 | 140 | 66 | 16 | 2.8 | 0.9 | 0.7 | 0.8 | 0.2 | 0.20 |
| 7 | CANCER | 2,558 | 1,267 | 695 | 239 | 148 | 58 | 14 | 2.7 | 1.2 | 1.3 | 1.1 | 0.4 | 0.10 |
| 8 | CANCER | 2,639 | 1,071 | 671 | 180 | 137 | 48 | 16 | 2.3 | 0.2 | 1.1 | 1.7 | 1.1 | 0.20 |
| 9 | CANCER | 2,650 | 1,539 | 873 | 214 | 125 | 63 | 17 | 2.9 | 2.1 | 0.9 | 0.9 | 0.5 | 0.20 |
| 10 | CANCER | 2,563 | 1,870 | 798 | 185 | 122 | 39 | 16 | 4.2 | 3.5 | 0.9 | 0.7 | 0.2 | 0.10 |
| 11 | CANCER | 2,632 | 1,460 | 740 | 219 | 138 | 66 | 14 | 3.2 | 28.0 | 1.4 | 1.0 | 0.1 | 0.10 |
| 12 | CANCER | 2,507 | 1,378 | 701 | 207 | 115 | 51 | 16 | 3.1 | 1.3 | 1.0 | 0.6 | 1.5 | 0.10 |
| 13 | CONTROL | 3,160 | 1,368 | 1,256 | 247 | 148 | 69 | 21 | 2.2 | 1.5 | 1.3 | 1.0 | 0.4 | 0.13 |
| 14 | CONTROL | 3,213 | 1,595 | 1,295 | 301 | 159 | 53 | 20 | 18.3 | 1.4 | 0.8 | 0.7 | 0.3 | 0.17 |
| 15 | CONTROL | 4,689 | 1,628 | 1,994 | 329 | 211 | 89 | 28 | 8.6 | 2.8 | 1.4 | 1.2 | 1.5 | 0.25 |
| 16 | CONTROL | 3,170 | 1,284 | 1,264 | 234 | 133 | 45 | 19 | 3.4 | 1.3 | 0.8 | 0.9 | 2.6 | 0.12 |
| 17 | CONTROL | 3,180 | 950 | 1,365 | 221 | 145 | 54 | 20 | 1.8 | 1.7 | 0.9 | 1.1 | 1.7 | 0.15 |
| 18 | CONTROL | 3,289 | 1,438 | 1,484 | 222 | 144 | 53 | 20 | 2.5 | 1.6 | 0.9 | 0.7 | 1.3 | 0.13 |
| 19 | CONTROL | 3,227 | 1,342 | 1,177 | 228 | 139 | 51 | 22 | 2.2 | 1.0 | 1.1 | 1.1 | 0.6 | 0.12 |
| 20 | CONTROL | 3,251 | 1,367 | 1,323 | 268 | 155 | 67 | 22 | 2.6 | 1.4 | 1.7 | 0.7 | 0.3 | 0.18 |
| 21 | CONTROL | 3,234 | 1,123 | 1,356 | 230 | 152 | 65 | 21 | 3.0 | 1.9 | 0.9 | 0.8 | 1.9 | 0.15 |
| 22 | CONTROL | 4,525 | 2,524 | 1,900 | 344 | 211 | 69 | 30 | 119.3 | 3.2 | 1.6 | 1.4 | 0.0 | 0.21 |
| 23 | CONTROL | 2,589 | 1,431 | 813 | 169 | 127 | 64 | 17 | 2.7 | 2.3 | 1.2 | 0.9 | 0.3 | 0.10 |
| 24 | CONTROL | 2,600 | 2,137 | 718 | 188 | 143 | 66 | 17 | 3.9 | 1.6 | 1.4 | 0.8 | 0.9 | 0.20 |
| 25 | CONTROL | 2,668 | 1,598 | 1,667 | 257 | 133 | 52 | 19 | 17.3 | 1.1 | 0.8 | 0.9 | 0.2 | 0.20 |
| 26 | CONTROL | 2,593 | 1,608 | 922 | 197 | 139 | 55 | 17 | 5.0 | 6.6 | 1.2 | 0.9 | 1.8 | 0.20 |
| 27 | CONTROL | 2,667 | 1,617 | 767 | 174 | 143 | 62 | 18 | 4.4 | 0.8 | 0.7 | 0.8 | 0.1 | 0.20 |
| 28 | CONTROL | 2,683 | 1,364 | 942 | 450 | 128 | 67 | 19 | 2.7 | 0.7 | 1.3 | 1.1 | 0.4 | 0.20 |
| 29 | CONTROL | 2,579 | 1,460 | 920 | 170 | 143 | 72 | 16 | 2.9 | 0.7 | 1.1 | 0.7 | 0.6 | 0.20 |
| 30 | CONTROL | 2,627 | 1,798 | 2,190 | 157 | 151 | 49 | 17 | 4.3 | 1.8 | 1.1 | 1.2 | 0.3 | 0.20 |

FIG. 9

DATA ANALYSIS RESULT OF THIS TIME (SECOND BLOOD SAMPLING)

| TRACE ELEMENT (ppm) | CONTROL (8 PERSONS) | | CANCER (12 PERSONS) | | P-VALUE |
|---|---|---|---|---|---|
| | MEAN | STANDARD DEVIATION | MEAN | STANDARD DEVIATION | |
| Na | 2625.8 | 41.44 | 2651.3 | 115.86 | 0.497 |
| Cl | 1626.6 | 246.73 | 1529.5 | 219.65 | 0.384 |
| S | 1117.4 | 525.82 | 807.8 | 94.44 | 0.143 |
| P | 220.3 | 97.84 | 263.2 | 102.87 | 0.361 |
| K | 138.4 | 8.37 | 131.3 | 10.11 | 0.105 |
| Ca | 60.9 | 8.04 | 57.3 | 9.62 | 0.386 |
| Mg | 17.5 | 1.07 | 16.3 | 1.44 | 0.053 |
| Br | 5.4 | 4.88 | 3.3 | 0.65 | 0.273 |
| Fe | 1.95 | 1.97 | 5.05 | 8.87 | 0.265 |
| Zn | 1.10 | 0.24 | 0.96 | 0.22 | 0.198 |
| Cu | 0.91 | 0.16 | 0.98 | 0.28 | 0.541 |
| Ti | 0.57 | 0.56 | 0.48 | 0.44 | 0.689 |
| Rb | 0.19 | 0.04 | 0.14 | 0.05 | 0.031 |

FIG. 10

DATA ANALYSIS RESULT OF FIRST AND SECOND BLOOD SAMPLING

| TRACE ELEMENT (ppm) | CONTROL (18 PERSONS) | | CANCER (12 PERSONS) | | P-VALUE |
|---|---|---|---|---|---|
| | MEAN | STANDARD DEVIATION | MEAN | STANDARD DEVIATION | |
| Na | 3108.0 | 617.67 | 2651.3 | 115.86 | 0.001 |
| Cl | 1535.1 | 356.57 | 1529.5 | 219.65 | 0.958 |
| S | 1297.4 | 427.29 | 807.8 | 94.44 | 0.0002 |
| P | 243.7 | 74.42 | 263.2 | 102.87 | 0.579 |
| K | 150.2 | 23.76 | 131.3 | 10.11 | 0.006 |
| Ca | 61.22 | 10.71 | 57.3 | 9.62 | 0.310 |
| Mg | 20.17 | 3.70 | 16.3 | 1.44 | 0.006 |
| Br | 11.51 | 27.34 | 3.3 | 0.65 | 0.222 |
| Fe | 1.86 | 1.36 | 5.05 | 8.87 | 0.241 |
| Zn | 1.12 | 0.29 | 0.96 | 0.22 | 0.087 |
| Cu | 0.94 | 0.21 | 0.98 | 0.28 | 0.709 |
| Ti | 0.84 | 0.76 | 0.48 | 0.44 | 0.105 |
| Rb | 0.17 | 0.04 | 0.14 | 0.05 | 0.095 |

FIG. 11

DISCRIMINANT ANALYSIS RESULT

1) SECOND TIME DATA (CONTROL: 8, CANCER PATIENT: 12)

METAL : S, P, Mg, Zn, Cu, Ti, Rb

|  | CON (PRED) | PAT (PRED) | TOTAL |
|---|---|---|---|
| CONTROL (ACTUAL) | 8 | 0 | 8 |
| PATIENT (ACTUAL) | 1 | 11 | 12 |
| TOTAL | 9 | 11 | 20 |

SENSITIVITY=91.7%(11/12), SPECIFICITY=100%(8/8)

2) FIRST & SECOND TIMES DATA (CONTROL: 18, CANCER PATIENT: 12)

METAL : S, P, Mg, Zn, Cu, Ti, Rb

|  | CON (PRED) | PAT (PRED) | TOTAL |
|---|---|---|---|
| CONTROL (ACTUAL) | 16 | 2 | 18 |
| PATIENT (ACTUAL) | 1 | 11 | 12 |
| TOTAL | 17 | 13 | 30 |

SENSITIVITY=91.7%(11/12), SPECIFICITY=88.9%(16/18)

CON (PRED) =CONTROL (PREDICTIVE)    PAT (PRED) =PATIENT (PREDICTIVE)

FIG. 13

DISCRIMINANT SCORE

| GROUP | CRITERION VARIABLE VALUE/RANGE |
|---|---|
| 1 | CONTROL |
| 2 | CASE |

[DISCRIMINANT SCORE LIST]

| No. | GROUP: ACTUAL | GROUP: PREDICTIVE | DISCRIMINANT SCORE |
|---|---|---|---|
| 1 | 1 | 1 | 1.062593 |
| 2 | 1 | 1 | 0.788588 |
| 3 | 1 | 1 | 8.334459 |
| 4 | 1 | 1 | 1.845479 |
| 5 | 1 | 1 | 1.588518 |
| 6 | 1 | 1 | 3.289605 |
| 7 | 1 | 1 | 0.157278 |
| 8 | 1 | 1 | 5.241326 |
| 9 | 1 | 1 | 3.595670 |
| 10 | 1 | 1 | 5.432528 |
| 11 | 2 | 2 | -4.433830 |
| 12 | 2 | 2 | -2.595352 |
| 13 | 2 | 2 | -4.259839 |
| 14 | 2 | 2 | -5.786881 |
| 15 | 2 | 2 | -3.589664 |
| 16 | 2 | 2 | -1.970507 |
| 17 | 2 | 2 | -4.572897 |
| 18 | 2 | 2 | -4.177352 |
| 19 | 2 | 2 | -0.619484 |
| 20 | 2 | 2 | -2.232609 |
| 21 | 2 | 2 | -3.613970 |
| 22 | 2 | 1 | -0.509301 |
| 23 | 1 | 2 | -1.560380 |
| 24 | 1 | 1 | 1.789240 |
| 25 | 1 | 1 | 1.975683 |
| 26 | 1 | 1 | 2.350742 |
| 27 | 1 | 1 | -0.430854 |
| 28 | 1 | 2 | -2.646223 |
| 29 | 1 | 1 | 1.673400 |
| 30 | 1 | 1 | 4.274034 |

MODIFICATION OF
CANCER EVALUATION METHOD OF INVENTION

MODIFICATION OF
CANCER EVALUATION SYSTEM OF INVENTION

FIG. 16

BY-GROUP, BY-PART, BY-GENDER SUBJECT NUMBER

| DIVISION | GENDER | ORDINARY PERSON | COLON CANCER | BREAST CANCER | PROSTATE CANCER | TOTAL |
|---|---|---|---|---|---|---|
| CONTROL | MALE | 30 | | | | 30 |
| | FEMALE | 30 | | | | 30 |
| CASE | MALE | | 43 | | 18 | 61 |
| | FEMALE | | 20 | 30 | | 50 |
| TOTAL | | 60 | 63 | 30 | 18 | 171 |

FIG. 17

ESSENTIAL ELEMENTS LIST

| | MALE | | FEMALE | |
|---|---|---|---|---|
| | COLON CANCER | PROSTATE CANCER | COLON CANCER | BREAST CANCER |
| Na | | | | |
| Mg | | | | |
| Al | | | | |
| P | ↑ | ↓ | ↓ | |
| K | | | | |
| Ca | | ↓ | ↓ | ↑ |
| Ti | | | | ↑ |
| Mn | | | ↑ | ↑ |
| Fe | | | | ↑ |
| Cu | | | | |
| Zn | | ↑ | | ↑ |
| Se | | | | |
| Rb | | | ↓ | ↓ |
| Ag | ↑ | | | |
| Sn | ↑ | ↑ | ↑ | |
| S | ↑ | ↓ | | |

↑ : CANCER PATIENT IS SIGNIFICANTLY HIGHER ($P<0.05$)

↓ : CANCER PATIENT IS SIGNIFICANTLY LOWER ($P<0.05$)

FIG. 18

DISCRIMINANT ANALYSIS RESULT (MALE)

1. MALE/PROSTATE CANCER
■PRIOR PROBABILITY OF GROUPS

| CASE2 CONTROL1 | PRIOR PROB. | CASES USED ** | |
|---|---|---|---|
| | | UNWEIGHTED | WEIGHTED |
| CONTROL | .500 | 30 | 30.000 |
| CANCER P. | .500 | 19 | 19.000 |
| TOTAL | 1.000 | 49 | 49.000 |

■CLASSIFICATION RESULT

| | | CASE2 CONTROL1 | PREDICTION * | | TOTAL |
|---|---|---|---|---|---|
| | | | CONTROL | CANCER P. | |
| ACTUAL DATA | FREQ. | CONTROL | 30 | 0 | 30 |
| | | CANCER P. | 2 | 16 | 18 |
| | % | CONTROL | 100.0 | .0 | 100.0 |
| | | CANCER P. | 11.1 | 88.9 | 100.0 | a. 95.8% OF GROUPED ORIGINAL CASES WERE CLASSIFIED CORRECTLY.

2. MALE/COLON CANCER
■PRIOR PROBABILITY OF GROUPS

| CASE2 CONTROL1 | PRIOR PROB. | CASES USED ** | |
|---|---|---|---|
| | | UNWEIGHTED | WEIGHTED |
| CONTROL | .500 | 30 | 30.000 |
| CANCER P. | .500 | 43 | 43.000 |
| TOTAL | 1.000 | 73 | 73.000 |

■CLASSIFICATION RESULT

| | | CASE2 CONTROL1 | PREDICTION * | | TOTAL |
|---|---|---|---|---|---|
| | | | CONTROL | CANCER P. | |
| ACTUAL DATA | FREQ. | CONTROL | 26 | 4 | 30 |
| | | CANCER P. | 4 | 39 | 43 |
| | % | CONTROL | 86.7 | 13.3 | 100.0 |
| | | CANCER P. | 9.3 | 90.7 | 100.0 | a. 89.0% OF GROUPED ORIGINAL CASES WERE CLASSIFIED CORRECTLY.

(**) CASES USED IN ANALYSIS
(*) PREDICTION BY DISCRIMINANT

CANCER P.: CANCER PATIENT
FREQ.: FREQUENCY
PRIOR PROB.: PRIOR PROBABILITY

FIG. 19

DISCRIMINANT ANALYSIS RESULT (FEMALE)

1. FEMALE/COLON CANCER

■PRIOR PROBABILITY OF GROUPS

| CASE2 CONTROL1 | PRIOR PROB. | CASES USED ** | |
|---|---|---|---|
| | | UNWEIGHTED | WEIGHTED |
| CONTROL | .500 | 30 | 30.000 |
| CANCER P. | .500 | 20 | 20.000 |
| TOTAL | 1.000 | 50 | 50.000 |

■CLASSIFICATION RESULT

| | | CASE2 CONTROL1 | PREDICTION * | | TOTAL |
|---|---|---|---|---|---|
| | | | CONTROL | CANCER P. | |
| ACTUAL DATA | FREQ. | CONTROL | 29 | 1 | 30 |
| | | CANCER P. | 2 | 18 | 20 |
| | % | CONTROL | 96.7 | 3.3 | 100.0 |
| | | CANCER P. | 10.0 | 90.0 | 100.0 | a. 94.0% OF GROUPED ORIGINAL CASES WERE CLASSIFIED CORRECTLY.

2. FEMALE/BREAST CANCER

■PRIOR PROBABILITY OF GROUPS

| CASE2 CONTROL1 | PRIOR PROB. | CASES USED ** | |
|---|---|---|---|
| | | UNWEIGHTED | WEIGHTED |
| CONTROL | .500 | 30 | 30.000 |
| CANCER P. | .500 | 30 | 30.000 |
| TOTAL | 1.000 | 60 | 60.000 |

■CLASSIFICATION RESULT

| | | CASE2 CONTROL1 | PREDICTION * | | TOTAL |
|---|---|---|---|---|---|
| | | | CONTROL | CANCER P. | |
| ACTUAL DATA | FREQ. | CONTROL | 30 | 0 | 30 |
| | | CANCER P. | 2 | 28 | 30 |
| | % | CONTROL | 100.0 | .0 | 100.0 |
| | | CANCER P. | 6.7 | 93.3 | 100.0 | a. 96.7% OF GROUPED ORIGINAL CASES WERE CLASSIFIED CORRECTLY.

(**) CASES USED IN ANALYSIS
(*) PREDICTION BY DISCRIMINANT

CANCER P.: CANCER PATIENT
FREQ.: FREQUENCY
PRIOR PROB.: PRIOR PROBABILITY

FIG. 22

■ PROSTATE CANCER

$D = +0.0903949 \times \text{AGE}$
$+0.0000053 \times \text{Na}$
$-0.0002593 \times \text{Mg}$
$+0.0000492 \times \text{Al}$
$-0.0000252 \times \text{P}$
$+0.0000105 \times \text{K}$
$+0.0000466 \times \text{Ca}$
$+0.0006909 \times \text{Ti}$
$+0.0154933 \times \text{Mn}$
$-0.0001292 \times \text{Fe}$
$-0.0027147 \times \text{Cu}$
$-0.0002606 \times \text{Zn}$
$+0.0166826 \times \text{Se}$
$-0.0077824 \times \text{Rb}$
$-0.0019460 \times \text{Ag}$
$+0.0193273 \times \text{Sn}$
$-0.0000003 \times \text{S}$
$-21.5837825 \text{ (CONSTANT)}$

■ COLON CANCER (MALE)

$D = +0.0136123 \times \text{AGE}$
$-0.0000011 \times \text{Na}$
$+0.0002178 \times \text{Mg}$
$-0.0000481 \times \text{Al}$
$+0.0000408 \times \text{P}$
$-0.0000249 \times \text{K}$
$-0.0000070 \times \text{Ca}$
$+0.0028095 \times \text{Ti}$
$+0.0115894 \times \text{Mn}$
$-0.0000653 \times \text{Fe}$
$-0.0001918 \times \text{Cu}$
$+0.0003566 \times \text{Zn}$
$+0.0127215 \times \text{Se}$
$+0.0050739 \times \text{Rb}$
$-0.0015596 \times \text{Ag}$
$-0.0154606 \times \text{Sn}$
$+0.0000001 \times \text{S}$
$-2.5979361 \text{ (CONSTANT)}$

FIG. 23

■BREAST CANCER
D = +0.0068043 × AGE
   +0.0000002 × Na
   −0.0001247 × Mg
   −0.0001381 × Al
   −0.0000210 × P
   +0.0000046 × K
   +0.0001442 × Ca
   +0.0093363 × Ti
   +0.0043409 × Mn
   +0.0000187 × Fe
   −0.0004532 × Cu
   −0.0007009 × Zn
   +0.0013783 × Se
   −0.0124300 × Rb
   +0.0006647 × Ag
   +0.0001697 × Sn
   +0.0000008 × S
   −10.0235054 (CONSTANT)

■COLON CANCER (FEMALE)
D = +0.0136123 × AGE
   −0.0000011 × Na
   −0.0002178 × Mg
   +0.0000481 × Al
   −0.0000408 × P
   +0.0000249 × K
   +0.0000070 × Ca
   +0.0028095 × Ti
   +0.0115894 × Mn
   −0.0000653 × Fe
   +0.0001918 × Cu
   −0.0003566 × Zn
   −0.0127215 × Se
   −0.0050739 × Rb
   −0.0015596 × Ag
   +0.0154606 × Sn
   −0.0000001 × S
   +2.5979361 (CONSTANT)

FIG. 24

COLON CANCER (MALE)

| DISCRIMINANT SCORE | NORMALITY PROBABILITY | CANCER PROBABLITY |
|---|---|---|
| 4.26113 | 0.99994 | 0.00006 |
| 2.71075 | 0.99755 | 0.00245 |
| 2.64777 | 0.99715 | 0.00285 |
| 2.62824 | 0.99701 | 0.00299 |
| 2.51741 | 0.99610 | 0.00390 |
| 2.34878 | 0.99416 | 0.00584 |
| 2.32378 | 0.99380 | 0.00620 |
| 2.15556 | 0.99074 | 0.00926 |
| 2.13823 | 0.99035 | 0.00965 |
| 2.09675 | 0.98935 | 0.01065 |
| 1.72989 | 0.97462 | 0.02538 |
| 1.63823 | 0.96855 | 0.03145 |
| 1.52412 | 0.95902 | 0.04098 |
| 1.50855 | 0.95752 | 0.04248 |
| 1.40987 | 0.94674 | 0.05326 |
| 1.36239 | 0.94067 | 0.05933 |
| 1.25759 | 0.92493 | 0.07507 |
| 1.25529 | 0.92454 | 0.07546 |
| 1.18552 | 0.91196 | 0.08804 |
| 1.18157 | 0.91119 | 0.08881 |
| 1.13851 | 0.90244 | 0.09756 |
| 1.07806 | 0.88885 | 0.11115 |
| 0.77816 | 0.79530 | 0.20470 |
| 0.73266 | 0.77690 | 0.22310 |
| 0.70921 | 0.76696 | 0.23304 |
| 0.70274 | 0.76417 | 0.23583 |
| 0.59413 | 0.71386 | 0.28614 |
| 0.45574 | 0.64132 | 0.35868 |
| 0.31203 | 0.55852 | 0.44148 |
| 0.22743 | 0.50788 | 0.49212 |
| 0.04211 | 0.39782 | 0.60218 |
| -0.02762 | 0.35838 | 0.64162 |
| -0.04219 | 0.35036 | 0.64964 |
| -0.05852 | 0.34146 | 0.65854 |
| -0.10601 | 0.31624 | 0.68376 |
| -0.12809 | 0.30486 | 0.69514 |
| -0.18557 | 0.27636 | 0.72364 |
| -0.34736 | 0.20553 | 0.79447 |
| -0.39093 | 0.18894 | 0.81106 |
| -0.39535 | 0.18732 | 0.81268 |
| -0.42743 | 0.17584 | 0.82416 |
| -0.54597 | 0.13822 | 0.86178 |
| -0.56432 | 0.13305 | 0.86695 |
| -0.57239 | 0.13082 | 0.86918 |
| -0.69106 | 0.10162 | 0.89838 |
| -0.69409 | 0.10095 | 0.89905 |
| -0.88548 | 0.06615 | 0.93385 |
| -0.91651 | 0.06168 | 0.93832 |
| -1.03413 | 0.04719 | 0.95281 |
| -1.06483 | 0.04398 | 0.95602 |
| -1.07075 | 0.04338 | 0.95662 |
| -1.08313 | 0.04216 | 0.95784 |
| -1.14333 | 0.03669 | 0.96331 |
| -1.15770 | 0.03548 | 0.96452 |
| -1.19916 | 0.03222 | 0.96778 |
| -1.20195 | 0.03201 | 0.96799 |
| -1.29571 | 0.02571 | 0.97429 |
| -1.30046 | 0.02543 | 0.97457 |
| -1.32663 | 0.02391 | 0.97609 |
| -1.33421 | 0.02349 | 0.97651 |
| -1.33555 | 0.02341 | 0.97659 |
| -1.35808 | 0.02221 | 0.97779 |
| -1.37049 | 0.02157 | 0.97843 |
| -1.39854 | 0.02019 | 0.97981 |
| -1.40132 | 0.02005 | 0.97995 |
| -1.53728 | 0.01454 | 0.98546 |
| -1.60681 | 0.01233 | 0.98767 |
| -1.79754 | 0.00782 | 0.99218 |
| -1.87906 | 0.00644 | 0.99356 |
| -2.37682 | 0.00195 | 0.99805 |
| -2.90785 | 0.00054 | 0.99946 |
| -2.90865 | 0.00054 | 0.99946 |
| -3.58334 | 0.00011 | 0.99989 |

FIG. 25

PROSTATE CANCER

| DISCRIMINANT SCORE | NORMALITY PROBABILITY | CANCER PROBABLITY |
|---|---|---|
| −3.91828 | 1.00000 | 0.00000 |
| −2.83060 | 1.00000 | 0.00000 |
| −2.55968 | 1.00000 | 0.00000 |
| −2.42911 | 0.99999 | 0.00001 |
| −2.41444 | 0.99999 | 0.00001 |
| −2.40018 | 0.99999 | 0.00001 |
| −2.26829 | 0.99999 | 0.00001 |
| −2.20148 | 0.99998 | 0.00002 |
| −2.06408 | 0.99997 | 0.00003 |
| −1.99179 | 0.99996 | 0.00004 |
| −1.96462 | 0.99996 | 0.00004 |
| −1.93831 | 0.99995 | 0.00005 |
| −1.91920 | 0.99995 | 0.00005 |
| −1.84619 | 0.99993 | 0.00007 |
| −1.79468 | 0.99991 | 0.00009 |
| −1.72974 | 0.99988 | 0.00012 |
| −1.64717 | 0.99983 | 0.00017 |
| −1.58259 | 0.99978 | 0.00022 |
| −1.45881 | 0.99964 | 0.00036 |
| −1.35360 | 0.99944 | 0.00056 |
| −1.12337 | 0.99856 | 0.00144 |
| −1.09644 | 0.99839 | 0.00161 |
| −0.87852 | 0.99605 | 0.00395 |
| −0.75881 | 0.99355 | 0.00645 |
| −0.74684 | 0.99323 | 0.00677 |
| −0.74559 | 0.99319 | 0.00681 |
| −0.29466 | 0.95786 | 0.04214 |
| −0.26188 | 0.95205 | 0.04795 |
| 0.11325 | 0.80871 | 0.19129 |
| 0.13739 | 0.79283 | 0.20717 |
| 0.32381 | 0.63954 | 0.36046 |
| 0.58782 | 0.37395 | 0.62605 |
| 0.60800 | 0.35468 | 0.64532 |
| 1.62390 | 0.00826 | 0.99174 |
| 1.77860 | 0.00438 | 0.99562 |
| 2.28952 | 0.00054 | 0.99946 |
| 2.47050 | 0.00025 | 0.99975 |
| 2.56395 | 0.00017 | 0.99983 |
| 2.76845 | 0.00007 | 0.99993 |
| 2.77136 | 0.00007 | 0.99993 |
| 2.88942 | 0.00005 | 0.99995 |
| 2.92863 | 0.00004 | 0.99996 |
| 3.06737 | 0.00002 | 0.99998 |
| 3.11103 | 0.00002 | 0.99998 |
| 3.14389 | 0.00002 | 0.99998 |
| 3.18904 | 0.00001 | 0.99999 |
| 3.25524 | 0.00001 | 0.99999 |
| 3.82273 | 0.00000 | 1.00000 |
| 4.77506 | 0.00000 | 1.00000 |

FIG. 26

BREAST CANCER (FEMALE)

| DISCRIMINANT SCORE | NORMALITY PROBABILITY | CANCER PROBABILITY |
|---|---|---|
| -2.98095 | 0.99998 | 0.00002 |
| -2.95453 | 0.99998 | 0.00002 |
| -2.93045 | 0.99997 | 0.00003 |
| -2.63524 | 0.99992 | 0.00008 |
| -2.61017 | 0.99992 | 0.00008 |
| -2.42915 | 0.99984 | 0.00016 |
| -2.30177 | 0.99975 | 0.00025 |
| -2.11123 | 0.99949 | 0.00051 |
| -2.04521 | 0.99936 | 0.00064 |
| -2.02333 | 0.99931 | 0.00069 |
| -1.87751 | 0.99883 | 0.00117 |
| -1.86025 | 0.99875 | 0.00125 |
| -1.81894 | 0.99856 | 0.00144 |
| -1.81507 | 0.99854 | 0.00146 |
| -1.80756 | 0.99850 | 0.00150 |
| -1.73916 | 0.99808 | 0.00192 |
| -1.70252 | 0.99781 | 0.00219 |
| -1.65372 | 0.99739 | 0.00261 |
| -1.59426 | 0.99677 | 0.00323 |
| -1.53140 | 0.99595 | 0.00405 |
| -1.48036 | 0.99514 | 0.00486 |
| -1.42753 | 0.99413 | 0.00587 |
| -1.39318 | 0.99336 | 0.00664 |
| -1.32500 | 0.99153 | 0.00847 |
| -1.24259 | 0.98865 | 0.01135 |
| -1.15700 | 0.98462 | 0.01538 |
| -1.13063 | 0.98311 | 0.01689 |
| -1.05834 | 0.97821 | 0.02179 |
| -0.86211 | 0.95685 | 0.04315 |
| -0.76118 | 0.93913 | 0.06087 |
| -0.42056 | 0.81932 | 0.18068 |
| -0.03411 | 0.53061 | 0.46939 |
| 0.08686 | 0.42257 | 0.57743 |
| 0.60041 | 0.10356 | 0.89644 |
| 0.73449 | 0.06659 | 0.93341 |
| 0.82726 | 0.04863 | 0.95137 |
| 0.86243 | 0.04310 | 0.95690 |
| 0.96700 | 0.03000 | 0.97000 |
| 0.99958 | 0.02678 | 0.97322 |
| 1.20722 | 0.01287 | 0.98713 |
| 1.22653 | 0.01202 | 0.98798 |
| 1.27632 | 0.01007 | 0.98993 |
| 1.37279 | 0.00714 | 0.99286 |
| 1.50423 | 0.00446 | 0.99554 |
| 1.79234 | 0.00159 | 0.99841 |
| 1.79358 | 0.00158 | 0.99842 |
| 2.01836 | 0.00071 | 0.99929 |
| 2.01972 | 0.00070 | 0.99930 |
| 2.06475 | 0.00060 | 0.99940 |
| 2.20638 | 0.00036 | 0.99964 |
| 2.28913 | 0.00027 | 0.99973 |
| 2.44711 | 0.00015 | 0.99985 |
| 2.53880 | 0.00011 | 0.99989 |
| 2.54333 | 0.00011 | 0.99989 |
| 2.54798 | 0.00011 | 0.99989 |
| 3.08437 | 0.00002 | 0.99998 |
| 3.15597 | 0.00001 | 0.99999 |
| 3.20250 | 0.00001 | 0.99999 |
| 3.65667 | 0.00000 | 1.00000 |
| 5.68891 | 0.00000 | 1.00000 |

FIG. 27

COLON CANCER (FEMALE)

| DISCRIMINANT SCORE | NORMALITY PROBABILITY | CANCER PROBABILITY |
|---|---|---|
| -3.24529 | 0.99997 | 0.00003 |
| -2.38315 | 0.99961 | 0.00039 |
| -2.13943 | 0.99921 | 0.00079 |
| -2.07780 | 0.99905 | 0.00095 |
| -2.06346 | 0.99901 | 0.00099 |
| -2.01036 | 0.99884 | 0.00116 |
| -1.75176 | 0.99753 | 0.00247 |
| -1.70081 | 0.99713 | 0.00287 |
| -1.65313 | 0.99671 | 0.00329 |
| -1.64231 | 0.99660 | 0.00340 |
| -1.53382 | 0.99533 | 0.00467 |
| -1.51476 | 0.99506 | 0.00494 |
| -1.35965 | 0.99224 | 0.00776 |
| -1.35369 | 0.99210 | 0.00790 |
| -1.25995 | 0.98963 | 0.01037 |
| -1.21155 | 0.98807 | 0.01193 |
| -1.20203 | 0.98773 | 0.01227 |
| -1.07693 | 0.98239 | 0.01761 |
| -0.89926 | 0.97069 | 0.02931 |
| -0.87592 | 0.96868 | 0.03132 |
| -0.82688 | 0.96400 | 0.03600 |
| -0.73886 | 0.95388 | 0.04612 |
| -0.66504 | 0.94336 | 0.05664 |
| -0.64175 | 0.93960 | 0.06040 |
| -0.27008 | 0.83939 | 0.16061 |
| -0.22095 | 0.81899 | 0.18101 |
| -0.08299 | 0.75113 | 0.24887 |
| -0.01011 | 0.70906 | 0.29094 |
| 0.00790 | 0.69803 | 0.30197 |
| 0.14702 | 0.60580 | 0.39420 |
| 0.26482 | 0.52099 | 0.47901 |
| 0.42470 | 0.40488 | 0.59512 |
| 0.60649 | 0.28524 | 0.71476 |
| 0.78774 | 0.18992 | 0.81008 |
| 0.98665 | 0.11566 | 0.88434 |
| 1.06033 | 0.09531 | 0.90469 |
| 1.09377 | 0.08718 | 0.91282 |
| 1.13290 | 0.07847 | 0.92153 |
| 1.20094 | 0.06519 | 0.93481 |
| 1.47117 | 0.03059 | 0.96941 |
| 1.64857 | 0.01840 | 0.98160 |
| 1.89601 | 0.00899 | 0.99101 |
| 2.23132 | 0.00338 | 0.99662 |
| 2.31515 | 0.00264 | 0.99736 |
| 2.34141 | 0.00245 | 0.99755 |
| 2.70948 | 0.00083 | 0.99917 |
| 3.16372 | 0.00022 | 0.99978 |
| 3.47359 | 0.00009 | 0.99991 |
| 3.59696 | 0.00006 | 0.99994 |
| 3.85111 | 0.00003 | 0.99997 |

CANCER EVALUATION METHOD AND CANCER EVALUATION SYSTEM

TECHNICAL FIELD

The present invention relates to a cancer evaluation method and a cancer evaluation system and more particularly, to a cancer evaluation method and a cancer evaluation system that utilize the concentration balance of elements (correlations among the concentrations of a set of evaluation elements) contained in a human serum.

BACKGROUND ART

As the diagnostic method of cancer, the method of direct observation or touching (e.g., palpation, endoscopic examination, etc.), the method of judging with images that reflect the inside of a human body (e.g., roentgenographic examination, CT examination, MRI examination, PET examination, etc.), and the method of examining blood or cells (e.g., blood test, cytodiagnosis, biopsy, etc.) are known.

However, the method of direct observation or touching has a disadvantage that the examination target (affected area) is restricted to breast, rectum, stomach, colon and so on. The method of judging with images has a disadvantage that not only that the detection sensitivity is low but also that the subject is exposed to radiation, although this method is readily carried out. On the other hand, the method of examining blood or cells is preferred because the burden on the patient is light and the detection sensitivity is high. In particular, if diagnosis is made possible by analyzing blood which is obtained from a patient, it is more preferred; this is because the burden on the patient is reduced to a low level and at the same time, diagnosis can be carried out even in the group or mass examination.

Conventionally, it is known that the concentrations of amino acids contained in the blood which is obtained from a patient vary in association with the onset of cancer. Patent Literature 1 discloses a method of diagnosing lung cancer by measuring the concentrations of in-blood amino acids of a patient utilizing such the relationship as described here. This method is an evaluation method of lung cancer characterized in that the step of obtaining amino acid concentration data about the values of the amino acid concentrations in the blood which is picked up from an evaluation subject, and the step of evaluating the concentration reference for evaluating the state of lung cancer of the evaluation subject based on the concentration values of Lys and His contained in the amino acid concentration data of the evaluation subject which is obtained in the step of obtaining amino acid concentration data are carried out. In addition, the step of evaluating the concentration reference may include the step of discriminating whether or not lung cancer develops with respect to the evaluation subject based on the concentration values of Lys and His contained in the amino acid concentration data of the evaluation subject which is obtained in the step of obtaining the amino acid concentration data. With the diagnosing method of Patent Literature 1, it is described that the state of lung cancer can be accurately evaluated utilizing the amino acid concentrations which are relevant to the state of lung cancer within the in-blood amino acid concentrations. (See Claims 1 and 2, Paragraph 0106, and FIGS. 1 to 3.)

On the other hand, it is known that the concentrations of trace elements contained in the blood have a relationship with the onset of cancer. For example, Non-Patent Literature 1 reports that the concentrations of copper (Cu) and zinc (Zn) and the concentration ratio of Cu/Zn in the serum of a breast cancer patient have a correlation with the development degree of condition of the patient. Moreover, Non-Patent Literature 2 reports that the concentration levels of cadmium (Cd) and lead (Pb) in the serum of a cancer patient are higher than those of a healthy person, and that the concentration levels of zinc (Zn), iron (Fe), and manganese (Mn) in the serum of a cancer patient are lower than those of a healthy person.

PRIOR ART LITERATURE

Patent Literature

[Patent Literature 1] Japanese Examined Patent Publication No. 5,470,848

Non-Patent Literature

[Non-Patent Literature 1] Gupta S K et al., Serum trace elements and Cu/Zn ratio in breast cancer patients, Journal of Surgical Oncology, March 46(3), 178-181, 1991

[Non-Patent Literature 2] Necip Pirincci et al., Levels of Serum Trace Elements in Renal Cell Carcinoma Cases, Asian Pacific Journal of Cancer Prevention, Vol. 14(1), 499-502, 2013

SUMMARY OF THE INVENTION

Problems to be Resolved by the Invention

With the diagnosing method of the aforementioned Patent Literature 1, since the amino acids in the blood degenerate early, there is a disadvantage that the amino acid concentrations need to be quickly measured after collecting the blood. Moreover, since the diagnosis cost is high, there is another disadvantage that the diagnosis service becomes expensive. On the other hand, the method of diagnosing cancer utilizing the trace element concentrations in the serum like the aforementioned Non-Patent Literatures 1 and 2 does not have the disadvantages of the diagnosing method of the Patent Literature 1 and therefore, the method utilizing the in-serum trace element concentrations is preferred.

As shown in FIG. 3, the "essential elements" that are essential for maintaining a human life consists of 12 major elements such as hydrogen (H), Carbon (C), . . . , and iron (Fe), and 16 trace elements such as boron (B), fluorine (F), . . . , and bromine (Br). It is known that in the case where any of the major elements and the trace elements is insufficient, a deficiency will occur, and that in the case where any of these elements is absorbed excessively, excess symptoms or poisoning symptoms will occur; this means that proper quantity needs to be absorbed at all times. The major elements are important as the constituents of a human body. The trace elements, which are utilized for the active centers of enzymes in substance metabolism in the human body and the like, is required slightly. It is said that if any of the trace elements is deficient or excessive, the balance of substance metabolism or the like in the human body is lost and as a result, peculiar symptoms for these respective elements will appear. On the other hand, it is also said that due to the onset of disease caused by physical deconditioning, disorder of the immune system, or the like, the composition of the trace elements changes and as a result, homeostasis will collapse. In addition, elements other than the "essential elements" shown in FIG. 3, e.g., titanium (Ti), rubidium (Rb), and so on, are contained in the blood of humans; the quantities of the elements excluding the "essential elements" also affect the maintenance of human life.

Moreover, the relationship between the biological significance of each element and cancer is shown in FIG. 4. As clearly seen from FIG. 4, the relationship of many of the elements with cancer is unknown. However, the inventors found the possibility that makes it possible to estimate the risk of suffering cancer by knowing the correlations among the in-serum concentrations of a specific set of elements based on the findings obtained from the inventors' researches and the information obtained from the articles and the like that have been reported so far; thereafter, the inventors created the present invention.

An object of the present invention is to provide a cancer evaluation method and a cancer evaluation system that make it possible to estimate the risk of suffering cancer of a subject with high accuracy and that do not have the disadvantages of early degeneration and high cost that arise in the case where the in-blood amino acid concentrations are utilized.

Another object of the present invention is to provide a cancer evaluation method and a cancer evaluation system that can be easily applied to group or mass examinations.

The other objects not specifically mentioned will become clear to those skilled in the art from the following description and drawings attached.

Means for Solving the Problems (1) According to the first aspect of the present invention, a cancer evaluation method is provided, which comprises:

the correlation operating step of operating a correlation among concentrations of a set of evaluation elements contained in a serum which is taken from a subject by applying concentration data of the set of evaluation elements to a discriminant function for discriminating which of a case group and a control group the subject belongs to; and the discriminating step of discriminating whether or not the subject suffers from any type of cancer based on the correlation operated in the correlation operating step.

The set of evaluation elements is determined appropriately according to the kind and/or concentration of the elements contained in the serum, the type of cancer which is to be discriminated, and so on.

With the cancer evaluation method according to the first aspect of the present invention, the concentration data of the set of evaluation elements are applied to the discriminant function for discriminating which of the case group and the control group the subject belongs to, thereby operating the correlation among the concentrations of the set of evaluation elements in the serum and then, whether or not the subject suffers from any type of cancer is discriminated based on the correlation thus obtained. Accordingly, the risk of suffering cancer of the subject can be estimated with high accuracy and at the same time, the disadvantages of early degeneration and high cost that arise in the case where the in-blood amino acid concentrations are utilized do not occur.

Moreover, after obtaining the concentration data of the set of evaluation elements in the serum which is taken from the subject, which of the case group and the control group the subject belongs to can be discriminated by automatic operation using a computer. Accordingly, the discrimination can be performed easily and quickly even if the number of the subjects is large, which means that the cancer evaluation method according to the first aspect of the present invention is easily applicable to group or mass examinations.

In a preferred embodiment of the cancer evaluation method according to the first aspect of the present invention, as the set of evaluation elements, a combination of elements are chosen such that Mahalanobis' generalized distance pertaining to the elements having their concentration data is maximized.

In another preferred embodiment of the cancer evaluation method according to the first aspect of the present invention, as the set of evaluation elements, a combination of 7 elements of S, P, Mg, Zn, Cu, Ti, and Rb is chosen.

In still another preferred embodiment of the cancer evaluation method according to the first aspect of the present invention, as the set of evaluation elements, a combination of elements are chosen such that the elements have their concentration data for a subject who belongs to the control group and a subject who belong to the case group. In this embodiment, the combination of all the elements that have their concentration data for the subject who belongs to the control group and the subject who belongs to the case group may be used as the set of evaluation elements, and the combination of a part of these elements may be used as the set of evaluation elements.

In a further preferred embodiment of the cancer evaluation method according to the first aspect of the present invention, as the set of evaluation elements, a combination of 16 elements of Na, Mg, Al, P, K, Ca, Ti, Mn, Fe, Zn, Cu, Se, Rb, Ag, Sn, and S is chosen.

In a further preferred embodiment of the cancer evaluation method according to the first aspect of the present invention, in the step of operating the correlation among the set of evaluation elements, age data of the subject is used in addition to the concentration data.

In a further preferred embodiment of the cancer evaluation method according to the first aspect of the present invention, the step of analyzing using a multiple logistic model (the onset probability operation step) is further included, wherein a probability that the subject will suffer from any type of cancer in his/her future is presented.

In a further preferred embodiment of the cancer evaluation method according to the first aspect of the present invention, in addition to discrimination whether or not the subject suffers from any type of cancer, discrimination of which type of cancer the subject has suffered from is carried out.

(2) According to the second aspect of the present invention, a cancer evaluation system is provided, which comprises:

a data storage section for storing concentration data of a set of evaluation elements contained in a serum which is taken from a subject;

a discriminant function generation section for generating a discriminant function for discriminating which of a case group and a control group the subject belongs to; and an evaluation result operation section for operating a correlation among concentrations of the set of evaluation elements contained in the serum by applying the concentration data of the subject stored in the data storage section to the discriminant function generated by the discriminant function generation section, thereby outputting an evaluation result that discriminates whether or not the subject suffers from any type of cancer based on the correlation.

The set of evaluation elements is determined appropriately according to the kind and/or concentration of the elements contained in the serum, the type of cancer which is to be discriminated, and so on.

With the cancer evaluation system according to the second aspect of the present invention, in the evaluation result operation section, the concentration data of the set of evaluation elements contained in the serum which is taken from the subject, which is stored in the data storage section, is applied to the discriminant function generated by the discriminant function generation section, thereby operating the correlation among the concentrations of the set of evaluation elements; then, the evaluation result that discriminates whether or not the subject suffers from any type of cancer is outputted based on the correlation thus operated. For this reason, the risk of suffering from cancer of the subject can be estimated with high accuracy and at the same time, the disadvantages of early degeneration and high cost that arise in the case where the in-blood amino acid concentrations are utilized do not occur.

Moreover, after obtaining the concentration data of the set of evaluation elements in the serum which is taken from the subject, which of the case group and the control group the subject belongs to can be discriminated by automatic operation using a computer. Therefore, the discrimination can be performed easily and quickly even if the number of the subjects is large, which means that the cancer evaluation system according to the second aspect of the present invention is easily applicable to group or mass examinations.

In a preferred embodiment of the cancer evaluation system according to the second aspect of the present invention, as the set of evaluation elements, a combination of elements are chosen such that Mahalanobis' generalized distance pertaining to the elements having their concentration data is maximized.

In another preferred embodiment of the cancer evaluation system according to the second aspect of the present invention, as the set of evaluation elements, a combination of 7 elements of S, P, Mg, Zn, Cu, Ti, and Rb is chosen.

In still another preferred embodiment of the cancer evaluation system according to the second aspect of the present invention, as the set of evaluation elements, a combination of elements are chosen such that the elements have their concentration data for a subject who belongs to the control group and a subject who belongs to the case group. In this embodiment, the combination of all the elements that have their concentration data for the subject who belongs to the control group and the subject who belongs to the case group may be used as the set of evaluation elements, and the combination of a part of these elements may be used as the set of evaluation elements.

In a further preferred embodiment of the cancer evaluation system according to the second aspect of the present invention, as the set of evaluation elements, a combination of 16 elements of Na, Mg, Al, P, K, Ca, Ti, Mn, Fe, Zn, Cu, Se, Rb, Ag, Sn, and S is chosen.

In a further preferred embodiment of the cancer evaluation system according to the second aspect of the present invention, in the evaluation result operation section, age data of the subject is used in addition to the concentration data.

In a further preferred embodiment of the cancer evaluation system according to the second aspect of the present invention, the evaluation result operation section analyzes using a multiple logistic model, thereby adding a probability that the subject will suffer from any type of cancer in his/her future to the evaluation result.

In a further preferred embodiment of the cancer evaluation system according to the second aspect of the present invention, the evaluation result operation section has a function of discriminating a type of cancer that has occurred in addition to a function of discriminating which of the control group and the case group the subject belongs to.

Advantageous Effects of the Invention

With the cancer evaluation method according to the first aspect of the present invention and the cancer evaluation system according to the second aspect of the present invention, there are advantageous effects that the risk of suffering cancer of a subject can be estimated with high accuracy, the disadvantages of early degeneration and high cost that arise in the case where the in-blood amino acid concentrations are utilized do not occur, and this method and this system can be applied easily to group or mass examinations.

BRIEF DESCRIPTION OF THE DRAWINGS

FIG. 3 is a table showing the list of the essential elements for a human body.

FIG. 4 is a table showing the relationship between the biological significance of the elements and cancer.

FIG. 5 is a table showing the measured data of the elements contained in the serums (samples) of 10 subjects, which are obtained in the preliminary examination.

FIG. 6A is a table showing the test result of the difference between the population means of the two groups (control group and case group), which are obtained using the measured data of the elements contained in the serums (samples) of 10 persons in the control group in the preliminary examination.

FIG. 6B is a table showing the test result of the difference between the population means of the two groups (control group and case group), which are obtained using the measured data of the elements contained in the serums (samples) of 10 persons in the control group in the preliminary examination, which is subsequent to FIG. 6A.

FIG. 7A shows tables showing the result of discriminant analysis for the measured data of the elements contained in the serums (samples) of the subjects in the cancer evaluation method according to the present invention.

FIG. 7B shows tables showing the result of discriminant analysis for the measured data of the elements contained in the serums (samples) of the subjects in the cancer evaluation method according to the present invention, which is subsequent to FIG. 7A.

FIG. 8 is a table showing the measured data of the elements contained in the serums (samples) of the 12 subjects in the case group and those of the 18 subjects in the control group, which is obtained in the cancer evaluation method according to the present invention.

FIG. 9 is a table showing the analysis result of the measured data of the elements contained in the serums (samples) of the 12 subjects in the case group and those of the 8 subjects in the control group, which is obtained in the cancer evaluation method according to the present invention.

FIG. 10 is a table showing the analysis result of the measured data of the elements contained in the serums (samples) of the 12 subjects in the case group and those of the 18 subjects in the control group, which is obtained in the cancer evaluation method according to the present invention.

FIG. 11 is tables showing the discrimination result about which of the control group and the case group the subjects belong to, which are obtained in the cancer evaluation method according to the present invention, which indicates the fact that the control group and the case group are discriminated with high accuracy.

FIG. 13 is a table showing the discriminant score obtained by discriminant analysis of the measured data of the elements contained in the serums (samples) of the subjects in the cancer evaluation method according to the present invention.

FIG. 16 is a table showing a breakdown of the subjects, wherein the concentrations of the 16 evaluation elements in the serums are measured using the modification (development) of the cancer evaluation method according to the present invention.

FIG. 17 is a concentration comparison table of the cancer patients and non-cancer patients based on the concentrations of the 16 evaluation elements in the serums which are measured using the modification (development) of the cancer evaluation method according to the present invention.

FIG. 18 shows tables showing the discrimination result of the prostate cancer patients (male) and the colon cancer patients (male) which are obtained in the modification (development) of the cancer evaluation method according to the present invention.

FIG. 19 shows tables showing the discrimination result of the colon cancer patients (female) and the breast cancer patients (female) which are obtained in the modification (development) of the cancer evaluation method according to the present invention.

FIG. 22 is an explanatory drawing showing an example of the discriminant for the prostate cancer patients (male) and the colon cancer patients (male) which are used in the modification (development) of the cancer evaluation method according to the present invention.

FIG. 23 is an explanatory drawing showing an example of the discriminant for the colon cancer patients (female) and the breast cancer patients (female) which are used in the modification (development) of the cancer evaluation method according to the present invention.

FIG. 24 is a table showing the discriminant score and the discriminant probability of the colon cancer patients (male) which are used in the modification (development) of the cancer evaluation method according to the present invention.

FIG. 25 is a table showing the discriminant score and the discriminant probability of the prostate cancer patients (male) which are used in the modification (development) of the cancer evaluation method according to the present invention.

FIG. 26 is a table showing the discriminant score and the discriminant probability of the breast cancer patients (female) which are used in the modification (development) of the cancer evaluation method according to the present invention.

FIG. 27 is a table showing the discriminant score and the discriminant probability of the colon cancer patients (female) which are used in the modification (development) of the cancer evaluation method according to the present invention.

EMBODIMENTS FOR CARRYING OUT THE INVENTION

Figure 1:
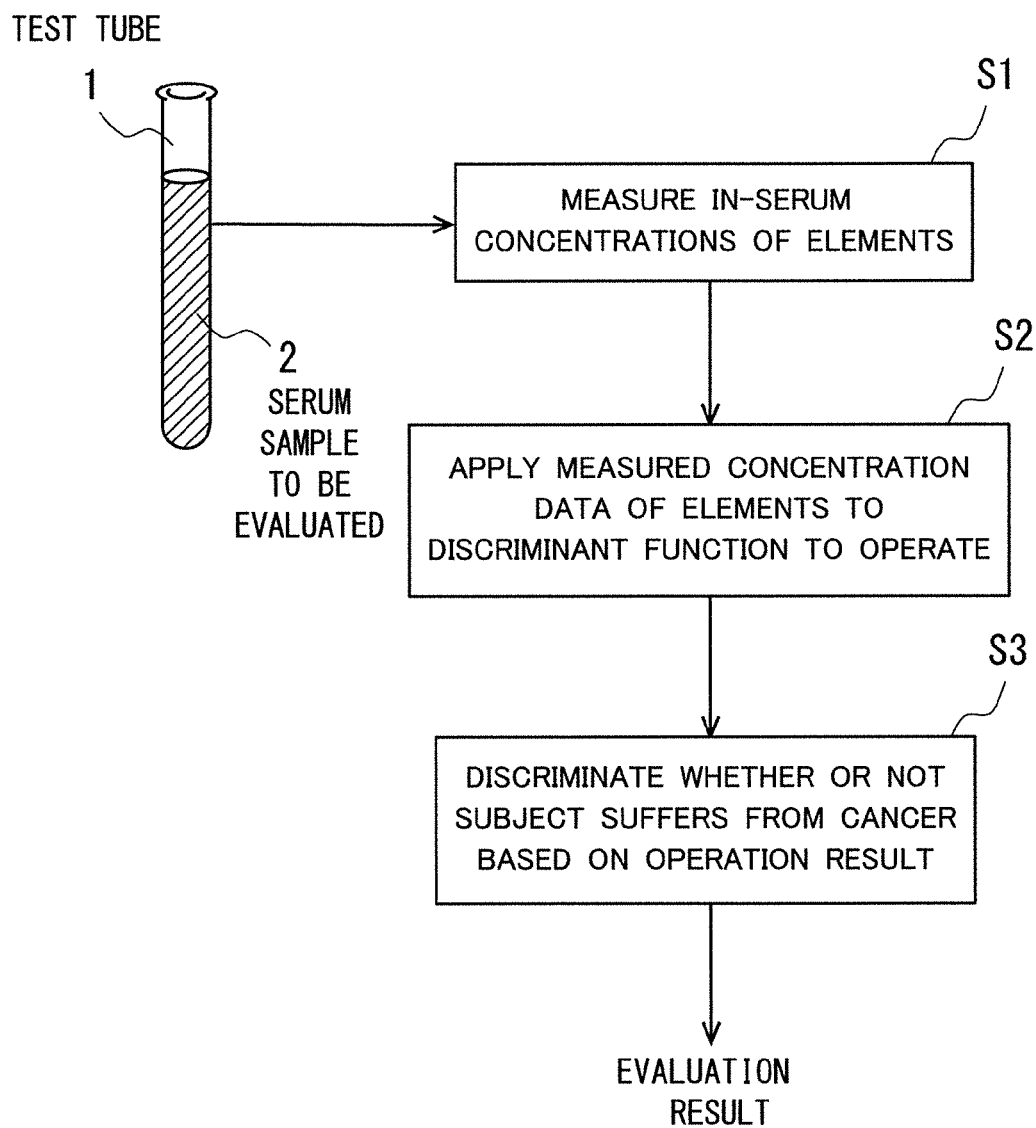
FIG. 1 is a flowchart showing the basic principle of the cancer evaluation method according to the present invention.

Preferred embodiments of the present invention will be described below in detail while referring to the drawings attached.

[Basic Principle of Cancer Evaluation Method of Invention]

The inventors conducted research earnestly to develop a new cancer screening method that uses the concentrations (contents) of the elements contained in the serum of a subject and as a result, obtained the following findings: The first finding is that the risk of suffering from cancer seems to be able to be estimated based on the concentration change of the elements by comparing the concentrations of the elements contained in the serums of cancer patients and in the serums of healthy persons (ordinary persons who were judged to have no cancer at the time of receiving a cancer examination). The second finding is that Inductively-Coupled Plasma Mass Spectrometry (ICP-MS), which has been popularly used in the semiconductor fields, seems to be applicable to measuring the in-serum concentrations of the elements.

Accordingly, based on the aforementioned two findings, firstly, the inventors conducted a preliminary examination twice in order to choose the elements to be measured as "a set of evaluation elements".

First Preliminary Examination: To find the optimal measurement condition for measuring the elements in the serum, 10 serums in the control group were used. These serums were mixed with nitric acid and then, proteins and amino acids were decomposed by heating the serums at a temperature in the range of 180° C. to 200° C. in a sealed pressure container in which metal contamination was suppressed, and subjected to a pretreatment in order to prevent hindrances to the concentration measurement of the elements in the serums. Thereafter, the serums were diluted to a predetermined concentration using ultrapure water containing no metal contamination. The concentrations of the 75 elements contained in the processed liquid thus obtained were measured utilizing Inductively-Coupled Plasma Mass Spectrometry (ICP-MS), the measurement result of which is shown in FIG. 5. In FIG. 5, the concentrations (unit: ppb) of the elements of Na, Cl, S, P, K, Ca, Mg, Br, Si, Fe, Zn, Cu, Ti, Rb, B, Se, Li, Al, I, Sr, Ge, Ba, Ni, As, Sb, Mo, Hg, Mn, Cs, Pt, Co, W, Th, Ti, and U are shown for the 10 samples.

To measure the concentrations of various elements, Inductively-Coupled Plasma Optical Emission Spectroscopy (ICP-OES), Inductively-Coupled Plasma Mass Spectroscopy (ICP-MS), Atomic Absorption Spectrometry (AAS), X-Ray Fluorescence analysis (XRF) and so on can be used in addition to ICP-MS. The reason why the inventors chose ICP-MS is that ICP-MS is recognized to be the simplest way where the quantitativity in measurement result is strict. Accordingly, if this condition is changed, or any other analyzing method that is more preferred is developed, it is needless to say that any other method than ICP-MS may be used for this purpose.

Second Preliminary Examination: Under the optimal condition found in the first preliminary examination, the contents of the 75 elements contained in the new 8 serums in the control group which were different from those used in the first preliminary examination and in the 12 serums in the case group were measured using ICP-MS. The breakdown of the 12 serums in the case group was that the numbers of lung cancer patients, breast cancer patients, colon cancer patients, and thyroid cancer patients are 2, 3, 3, and 2, respectively. Thereafter, the difference of the concentrations of the elements between the control group and the case group thus obtained was analyzed statistically.

The elements having their measured concentration values with respect to all the subjects (all the serums) were 14 elements of Na, Cl, S, P, K, Ca, Mg, Br, Si, Fe, Zn, Cu, Ti, and Rb among the concentration data of the 75 elements in the serums which were obtained in the second preliminary examination. Then, the 13 elements excluding Si (the reports showing that Si is concerned with vital functions have been scarcely made) among these 14 elements were chosen, and the concentrations of these 13 elements were analyzed statistically. In other words, the 13 elements of Na, Cl, S, P, K, Ca, Mg, Br, Fe, Zn, Cu, Ti, and Rb were chosen as the target elements for the statistical analysis. The result of the data analysis is shown in FIGS. 9 and 10. FIG. 9 shows the result of the second data analysis and FIG. 10 shows the result of the case where the results of the first and second data analyses are combined.

Using the concentration data of the aforementioned 13 elements, the element combination that makes it possible to discriminate best between the case group and the control group clearly was explored using a computer while changing the combinations of these 13 elements many times over. As a result, it was found that the discriminant ability was the highest in the case where the 7 elements of S, P, Mg, Zn, Cu, Ti, and Rb were combined and used as the "set of evaluation elements".

In this analysis, in order to clarify the elements that are concerned with the difference between the case group and the control group among the aforementioned 13 elements chosen, discriminant analysis and multiple logistic model were used, in which a combination that maximizes the difference between the combined elements was explored while taking the combinations of the elements into consideration. As a result, it was found that the differences among the combined elements were maximized in the case where the 7 elements of S, P, Mg, Zn, Cu, Ti, and Rb were combined and used as the "set of evaluation elements". In other words, it was found that the case group and the control group can be discriminated with high accuracy by measuring the in-serum concentrations of these 7 elements and analyzing statistically the measurement result thus obtained. Because of this finding, it was made clear that a new method of diagnosing the presence and absence of the onset of cancer in the human body was able to be developed.

Next, the detail of the aforementioned analysis will be explained below. First, the 13 elements (Na, Cl, S, P, K, Ca, Mg, Br, Fe, Zn, Cu, Ti, Rb) were chosen as the target elements, i.e., the "set of evaluation elements" and then, discriminant analysis was carried out for the two groups of the control group (0) and the case group (1). Concretely speaking, a test (t-test) for the difference between the population means of the control group and the case group was carried out. This was to search to what degree the discrimination between the two groups is affected by the 13 elements. The result of this test is shown in FIGS. 6A and 6B. These two figures show the result of reviewing the difference between the means of the two groups of the control group (0) and the case group (1) with respect to the 13 elements. When the difference between the two groups was compared with respect to the respective elements individually, significant differences ($P<0/01$) were found between the two groups with respect to the elements of Na, S, K, and Mg, which resulted in that the difference in the case group was lower than that in the control group. Although the difference was observed between these two groups with respect to the respective elements individually, the relationships among the elements were ignored in this analysis; therefore, it was found that this analysis included many problems if used for the purpose of evaluating the risk of disease. To solve these problems, it was necessary to execute analysis using multivariate analysis capable of considering the relationships among the elements, i.e., discriminant analysis. In addition, when the p-value that indicates the significance probability was 0.05 or less in FIGS. 6A and 6B, it was judged that the parameters were "significantly different".

Accordingly, next, a discriminant function was obtained in the following way. This was to analyze the concentration balance (correlations) among the elements. The concentrations of the individual elements included personal differences and were difficult to use as an indicator; therefore, the correlations of the concentrations among the elements were obtained here.

A discriminant function can be expressed in the following equation (1).

$$\text{Discriminant Value } (D) = \text{Function } (F) \text{ (Explanatory Variables 1 to } n, \text{ Discriminant Coefficients)} \quad (1)$$

(n is an integer equal to or greater than 2.)

Taking the weight (the influence on discrimination) of the respective explanatory variables 1 to n into consideration, the equation (1) can be written as the following equation (2).

$$\text{Discriminant Value}(D) = (\text{Discriminant Coefficient 1}) \times (\text{Explanatory Variable 1}) + (\text{Discriminant Coefficient 2}) \times (\text{Explanatory Variable 2}) + \ldots (\text{Discriminant Coefficient } n) \times (\text{Explanatory Variable } n) + \text{Constant} \quad (2)$$

Here, the 7 elements (S, P, Mg, Zn, Cu, Ti, Rb) which are chosen from the result of the test (t-test) for the difference between the population means of the two groups are defined as the explanatory variables and at the same time, the discriminant coefficients are used as the weight for these explanatory variables, resulting in a discriminant function. A desired discriminant function can be easily obtained by inputting the concentration values (concentration data) of the 7 elements into a known discriminant analysis program.

If the discriminant value (discriminant score) (D) calculated in this way is equal to 0 or less, it is judged that the subject belongs to the case group (1), and if the discriminant value (D) is equal to 0 or greater, it is judged that the subject belongs to the control group (2).

Next, to obtain the probability that the subject belongs to the case group (1) or the control group (2), analysis is carried out using the multiple logistic model, thereby obtaining the incidence. The incidence is given by the following equation (3) using the discriminant values (D) which is obtained in the aforementioned discriminant analysis.

$$\text{Incidence}=1/[1+\exp(-\text{Discriminant Value})] \quad (3)$$

Since the incidence can be obtained using the equation (3), the probability that the subject belongs to the case group (1) also can be obtained. This means that the subject can know his/her own current risk of suffering from cancer.

As a result of the discriminant function, the discriminant ability was the highest when the aforementioned 7 elements (S, P, Mg, Zn, Cu, Ti, Rb) are used. Table 1 of FIG. 7A shows the correlations among these 7 elements. For example, S of 1) has a strong positive correlation with Mg of 3) at the value of 0.714. This means that S and Mg have the relationship that Mg increases if S increases and Mg decreases if S decreases. The correlation coefficients shown in Table 1 of FIG. 7A indicate the individual relationships among the 7 elements.

Moreover, Mahalanobis' generalized distance shown in Table 2 of FIG. 7A indicates the distance between the barycenters of the case group (1) and the control group (2). If the magnitude of the Mahalanobis' generalized distance becomes larger, it can be represented that the difference between the two groups (1) and (2) is larger. The magnitude of Mahalanobis' generalized distance was maximized when the aforementioned 7 elements were used as the set of evaluation elements. For this reason, the equation obtained using the aforementioned 7 elements was determined as the final discriminant function in order to discriminate these two groups. Box's test in Table 3 of FIG. 7A shows that this discriminant is significant (meaningful) (P=0.004651).

Table 4 of FIG. 7B indicates the significance of the variables used in the discriminant analysis, Table 5 of FIG. 7B indicates the spurious percentage of correct classifications, and Table 6 of FIG. 7B indicates the barycenters of the respective groups in the discriminant space.

With the cancer evaluation method according to the present invention, the 7 elements (S, P, Mg, Zn, Cu, Ti, Rb) that were specified through the aforementioned two preliminary examinations are designated as the set of evaluation elements and then, the concentrations of these elements contained in the serum of a subject are measured, thereby evaluating whether or not the subject suffers from cancer.

Next, the basic principle of the cancer evaluation method according to the present invention will be explained below with reference to FIG. 1.

With the cancer evaluation method according to the present invention, as seen from FIG. 1, first, a serum sample 2 that has been collected from the subject is put into a test tube 1 and then, the sample 2 is placed in an analyzing apparatus and analyzed, thereby measuring the concentrations of the predetermined elements (the set of evaluation elements) in the serum (Step S1). The elements whose concentrations are to be measured here are the 7 elements of S, P, Mg, Zn, Cu, Ti, and Rb.

Next, the in-serum concentration data of the set of evaluation elements obtained in the step S1 are applied to a predetermined discriminant function to conduct an operation (Step S2).

Figure 12:
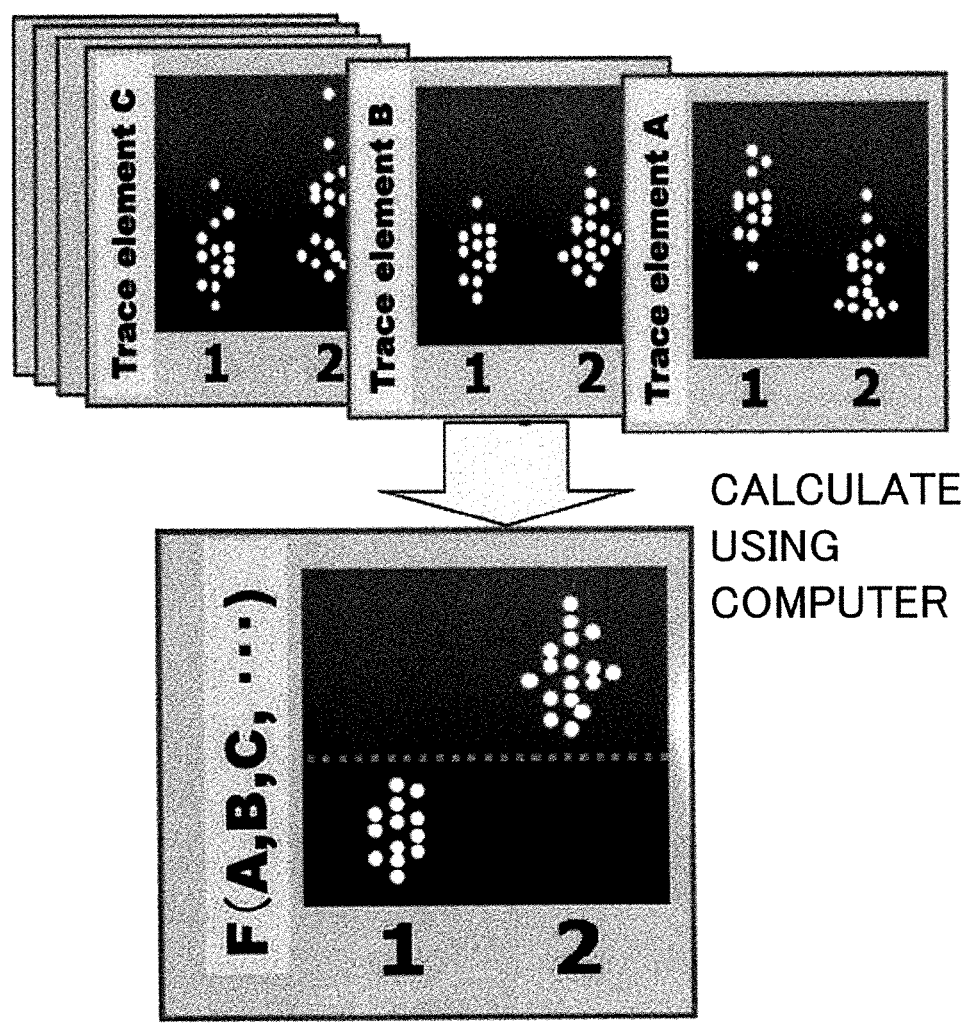
FIG. 12 is a conceptual diagram showing the fact that the discrimination result about which of the control group and the case group the subjects belong to can be obtained by integrating the discrimination results for the respective specific elements in the cancer evaluation method according to the present invention.

Finally, based on the operation result obtained in the step S2, whether or not the subject from which the serum sample 2 has been collected suffers from any type of cancer is discriminated. As a result, as shown in FIG. 12, a desired evaluation result about the presence or absence of the onset of cancer is obtained (Step S3).

With the cancer evaluation method according to the present invention, as explained above, the concentration data of the set of evaluation elements (S, P, Mg, Zn, Cu, Ti, Rb) in the serum collected from the subject are applied to the predetermined discriminant function, thereby operating the correlations among the concentrations of the set of evaluation elements. Thereafter, based on the correlations thus obtained, whether or not the subject suffers from any type of cancer is discriminated. Accordingly, the risk of suffering from cancer of the subject can be estimated with high accuracy and at the same time, the disadvantages of early degeneration and high cost that arise in the case where the in-blood amino acid concentrations are utilized do not occur.

Moreover, after obtaining the concentration data of the set of evaluation elements in the serum that has been taken from the subject, which of the case group and the control group the subject belongs to can be discriminated by automatic operation using a computer. Therefore, this method is easily applicable to group or mass examinations.

[Basic Structure of Cancer Evaluation System of Invention]

Next, the cancer evaluation system according to the present invention will be explained below.

Figure 2:
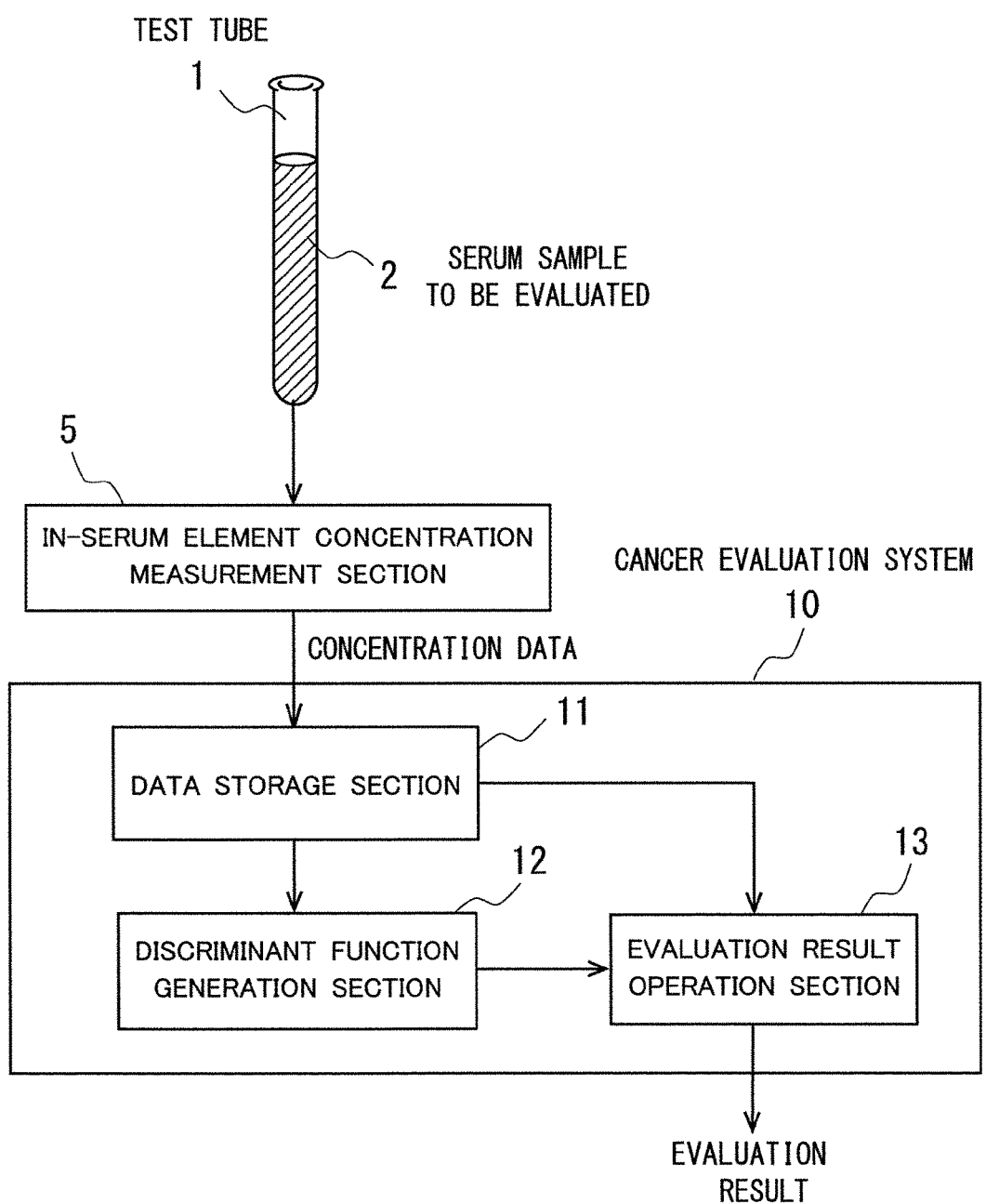
FIG. 2 is a functional block diagram showing the basic structure of the cancer evaluation system according to the present invention.

The basic structure of the cancer evaluation system 10 of the present invention is shown in FIG. 2. The cancer evaluation system 10, which is a system for carrying out the aforementioned cancer evaluation method of the present invention, comprises a data storage section 11, a discriminant function generation section 12, and an evaluation result operation section 13, as seen from FIG. 2.

An in-serum element concentration measurement section 5 is provided outside the cancer evaluation system 10, in which the in-serum concentrations of the set of evaluation elements (S, P, Mg, Zn, Cu, Ti, Rb) are measured using a serum sample 2 that has been collected from a subject and that has been put into a test tube 1. The concentration data of the set of evaluation elements thus obtained in the in-serum element concentration measurement section 5 are supplied to the data storage section 11. As the in-serum element concentration measurement section 5, for example, a known ICP mass spectrometer is used.

The data storage section 11 is a section for storing the concentration data of the set of evaluation elements obtained in the in-serum element concentration measurement section 5, which is usually formed by a known storage device.

The discriminant function generation section 12 is a section for generating a discriminant function that is used for the operation in the evaluation result operation section 13, which is usually formed to include a known program.

The evaluation result operation section 13 conducts the operation in a predetermined method. Based on the operation result outputted by the evaluation result operation section 13, a desired evaluation result is obtained, in other words, the presence or absence of the onset of cancer is evaluated.

When the aforementioned cancer evaluation method according to the present invention is carried out with the cancer evaluation system 10, the risk of suffering from cancer is calculated using, for example, pattern analysis of the in-serum concentrations of the set of evaluation elements, and the result that the possibility of having cancer is expressed stochastically based on the said risk is presented. Concretely speaking, serums (e.g., 0.5 cc) are collected at physical checkups which are conducted in medical institutions or diagnosis institutions and then, are subjected to concentration measurement of the set of specific evaluation elements (S, P, Mg, Zn, Cu, Ti, Rb) at inspection agencies. Thereafter, based on the concentration data of the set of evaluation elements measured at the inspection agencies, the risk of cancer is calculated at an institution like, for example, a risk evaluation center (provisional name). The calculation result of the risk thus obtained is delivered to blood collection agencies and then, sent to a medical examinee from the blood collection agencies. If the examinee is suspected to have cancer, the blood collection agencies recommend him/her to receive "existing cancer examination". The personal information is systemized so as not to reach the inspection agencies and the risk evaluation center through the encryption or consecutive numbering which is executed at the blood collection agencies.

[Modification of Cancer Evaluation Method of Invention]

Next, a modification of the cancer evaluation method of the present invention will be explained below. It can be said that this modification is a development of the cancer evaluation method of the present invention.

Figure 14:
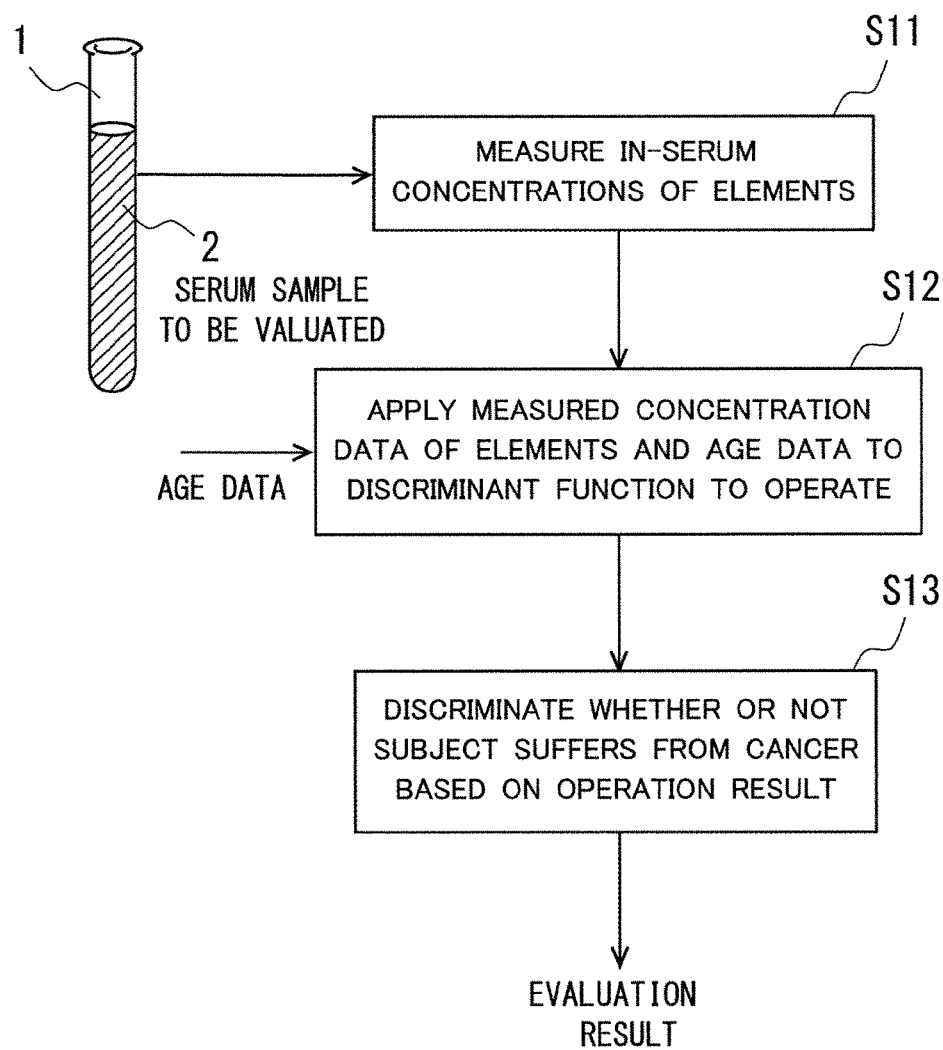
FIG. 14 is a flowchart showing a modification (development) of the cancer evaluation method according to the present invention.

The modification (development) of the cancer evaluation method of the present invention is shown in FIG. 14. With this cancer evaluation method of the present invention, as seen from FIG. 14, first, a serum sample 2 that has been collected from a subject is put into a test tube 1 and then, the sample 2 is placed in an analyzing apparatus and analyzed, thereby measuring the concentrations of the set of elements in the serum (Step S11). Here, the elements whose concentrations are to be measured are not limited; the concentrations of all the elements whose concentrations are measurable are measured. Moreover, (all or part of) the elements whose concentration data have been obtained in both the control group and the case group are designated as the set of evaluation elements. Concretely speaking, for example, 16 elements of Na, Mg, Al, P, K, Ca, Ti, Mn, Fe, Zn, Cu, Se, Rb, Ag, Sn, and S are designated as the set of evaluation elements. This modification (development) is different from the cancer evaluation method of the present invention shown in FIG. 1 at this point. The reason why (all or part of) the elements whose concentration data have been obtained in both the control group and the case group are designated as the set of evaluation elements is that these data can be utilized for a discriminant as stable data; in other words, if the concentration data observed in only the control group or those observed in only the case group are used for a discriminant, it is difficult to obtain a desired discrimination result.

Subsequently, the in-serum concentration data of the set of evaluation elements obtained in the step S11 and the age of the subject are applied to a predetermined discriminant function to conduct an operation (Step S12).

Finally, based on the operation result obtained in the step S2, whether or not the subject from which the serum sample 2 has been collected suffers from any type of cancer is discriminated. As a result, a desired evaluation result about the presence or absence of the onset of cancer is obtained (Step S13).

With the modification (development) of the cancer evaluation method of the present invention, as explained above, the concentration data of the set of evaluation elements (all or part of the elements whose concentration data have been obtained in both the control group and the case group) and the age of the subject are applied to the predetermined discriminant function and then, the correlations among the concentrations of the set of evaluation elements and the age are calculated. Thereafter, based on the correlations among the concentrations of the elements and the age thus obtained, whether or not the subject suffers from any type of cancer is discriminated. Accordingly, the risk of suffering cancer of the subject can be estimated with high accuracy and at the same time, the disadvantages of early degeneration and high cost that arise in the case where the in-blood amino acid concentrations are utilized do not occur.

Moreover, after obtaining the concentration data of the set of evaluation elements in the serum that has been taken from the subject, which of the case group and the control group the subject belongs to can be discriminated by automatic operation using a computer. Therefore, this modification (development) is easily applicable to group or mass examinations.

[Modification of Cancer Evaluation System of Invention]

Figure 15:
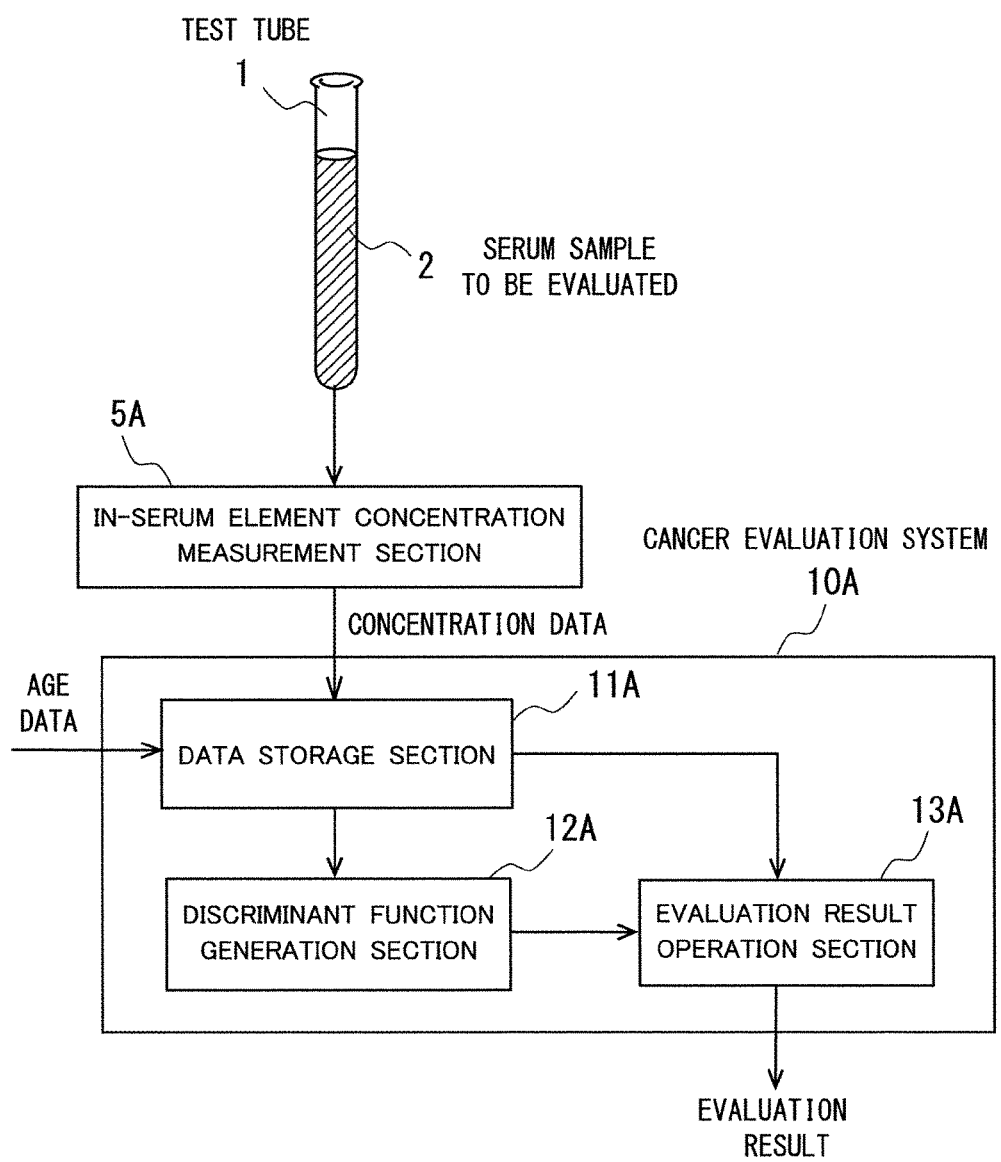
FIG. 15 is a functional block diagram showing a modification (development) of the cancer evaluation system according to the present invention.

The basic structure of a cancer evaluation system 10A, which is a modification (development) of the cancer evaluation system 10 of the present invention, is shown in FIG. 15. The cancer evaluation system 10A, which is a system for carrying out the aforementioned modification (development) of the cancer evaluation method of the present invention, comprises a data storage section 11A, a discriminant function generation section 12A, and an evaluation result operation section 13A, as seen from FIG. 15.

An in-serum element concentration measurement section 5A is provided outside the cancer evaluation system 10A, in which the in-serum concentrations of a set of evaluation elements (16 elements of Na, Mg, Al, P, K, Ca, Ti, Mn, Fe, Zn, Cu, Se, Rb, Ag, Sn, and S) are measured using a serum sample 2 that has been collected from a subject and that has been put into a test tube 1. The concentration data of the set of evaluation elements thus obtained in the in-serum element concentration measurement section 5A are supplied to the data storage section 11A. On the other hand, the age data of the subject also is supplied to the data storage section 11A. As the in-serum element concentration measurement section 5A, for example, a known ICP mass spectrometer is used.

The data storage section 11A is a section for storing the concentration data of the set of evaluation elements obtained in the in-serum element concentration measurement section 5A and the age data of the subject, which is usually formed by a known storage device.

The discriminant function generation section 12A is a section for generating a discriminant function that is used for the operation in the evaluation result operation section 13A, which is usually formed to include a known program.

The evaluation result operation section 13A conducts the operation in a predetermined method. Based on the operation result obtained in the evaluation result operation section 13A, a desired evaluation result is obtained, in other words, the presence or absence of the onset of cancer is evaluated.

When the modification (development) of the cancer evaluation method of the present invention is carried out, similar to the aforementioned cancer evaluation method of the present invention shown in FIG. 1, the risk of suffering from cancer is calculated using, for example, pattern analysis of the in-serum concentrations of the set of evaluation elements and then, the result that the possibility of having cancer is expressed stochastically based on the said risk is presented. Concretely speaking, the serum (e.g., 0.5 cc) is collected at physical checkups that are conducted in medical institutions or diagnosis institutions and then, is subjected to concentration measurement of the set of specific evaluation elements (16 elements of Na, Mg, Al, P, K, Ca, Ti, Mn, Fe, Zn, Cu, Se, Rb, Ag, Sn, and S) at inspection agencies. Thereafter, the risk of having cancer is calculated at an institution like, for example, a risk evaluation center (provisional name), based on the concentration data that are measured at the inspection agencies and the age data of the subject. The calculation result of the risk is delivered to blood collection agencies and then, sent to medical examinees from the blood collection agencies. If the examinee is suspected to have cancer, the blood collection agencies recommend him/her to receive "existing cancer examination". The personal information is systemized so as not to reach the inspection agencies and the risk evaluation center through the encryption or consecutive numbering which is executed at the blood collection agencies.

Example 1

Next, the present invention will be explained in more detail based on examples.

Example 1 corresponds to the cancer evaluation method of the present invention shown in FIG. 1.

Using the serums of the 8 subjects in the control group and those of the 12 subjects in the case group (20 subjects in total) used in the aforementioned second preliminary examination, the concentrations (contents) of the 7 elements (S, P, Mg, Zn, Cu, Ti, Rb) contained in these serums were measured by the ICP mass spectrometry and as a result, the result shown in FIG. 8 was obtained. In this example, the aforementioned 7 elements were the "set of evaluation elements". The breakdown of the 12 subjects in the case group was that the numbers of lung cancer patients, breast cancer patients, colon cancer patients, and thyroid cancer patients are 2, 3, 3, and 2, respectively. Thereafter, the difference of the concentrations of the elements thus obtained between the control group and the case group was analyzed statistically in the following way.

First, a test for the difference between the population means of the two groups (the control group and the case group) was carried out with respect to the serums (samples) of the 20 subjects and consequently, the result shown in FIGS. 6A and 6B was obtained. Next, the concentration data of the 7 elements contained in the serums (samples) of the 30 subjects were subjected to discriminant analysis and consequently, the result shown in FIGS. 7A and 7B was obtained. The discriminant score (discriminant value) shown in FIG. 13 was obtained. The discriminant function used for this purpose was as follows.

Discriminant value ($D$)=0.0040×(Concentration of S)−0.0133×(Concentration of P)+0.3336×(Concentration of Mg)+3.3637×(Concentration of Zn)−5.3088×(Concentration of Cu)+1.1833× (Concentration of Ti)+20.7033×(Concentration of Rb)−9.9368

The final result of the discriminant analysis shown in the upper table of FIG. 11 was obtained. As seen from this table, all the 8 samples in the control group were estimated to belong to the control group by the set of evaluation elements (S, P, Mg, Zn, Cu, Ti, Rb) used in this discrimination and at the same time, 11 out of the 12 samples in the case group (cancer patients) were estimated to belong to the case group and 1 out of the 12 samples in the case group was estimated to belong to the control group (healthy persons). From these results, it was found that the discriminant ability was that the sensitivity (which indicates the rate of actual patients to be judged patients) was 91% (11/12) and that the specificity (which indicates the rate of non-patients to be judged non-patients) was 100% (8/8).

It is ideal that the discriminant probability of the case group (cancer patients) is 100% in both of the sensitivity and the specificity. However, the sensitivity and the specificity of the screening methods (X-ray test for chest, barium test for stomach, fecal occult blood reaction for colon, and so on) that are being used in the current cancer check are approximately 80% each. Therefore, it is expected that the prediction (screening) method of suffering from cancer utilizing the difference between the concentration patterns of the specific in-serum elements, which was newly used here, will be a significant method.

Example 2

This Example also corresponds to the cancer evaluation method of the present invention shown in FIG. 1.

The same concentration measurement and the same discriminant analysis as those used in Example 1 were carried out except that the total number of the serums of the subjects in the control group which were used in the aforementioned second preliminary examination was increased to 18 from 8 by adding the serums of the subjects (10 subjects) in the control group which were used in the aforementioned first preliminary examination. The final result of the discriminant analysis shown in the lower table of FIG. 11 was obtained. The concentration data of the same elements as those of Example 1 were designated; the sensitivity was the same as that of Example 1 but the specificity was lowered to 88%.

Example 3

This Example corresponds to the modification (development) of the cancer evaluation method of the present invention shown in FIG. 14.

As shown in FIG. 16, the subjects was determined so that the control group (ordinary persons) includes 30 men and 30 women and the case group (cancer patients) includes 43 male patients with colon cancer, 20 female patients with colon cancer, 30 female patients with breast cancer, and 18 male patients with prostatic cancer. Then, the concentrations of all the elements contained in the serums of all the subjects using ICP mass spectrometry. 16 elements (Na, Mg, Al, P, K, Ca, Ti, Mn, Fe, Zn, Cu, Se, Rb, Ag, Sn, S) out of the 75 elements contained in the serums the concentrations of which were obtained in the aforementioned second preliminary examination had their measurement values of the concentrations with respect to all the subjects (all the serums). Accordingly, the data of the 17 items in total were formed by adding the age data of the subjects to the concentration data of these 16 elements and were used for analysis.

As the method of measuring the concentrations of various elements, ICP Optical Emission Spectroscopy (ICP-OES), ICP mass spectrometry (ICP-MS), Atomic Absorption Spectrometry (AAS), X-Ray Fluorescence analysis (XRF) and so on can be used. However, the measurement here was carried out using ICP mass spectrometry which was recognized to be the simplest way where the quantitativity in measurement result is strict.

If some difference was observed between the in-serum concentrations of the elements in the control group and those in the case group, it was estimated that these elements have some relationship with the onset of cancer. Therefore, a test for the difference between the means of the control group and the case group was carried out in order to review the difference between the control and case groups using the 16 elements excluding the age. As a result, the result shown in FIG. 17 was obtained. In FIG. 17, when the concentration of any of the elements in the case group is/are higher statistically significantly, the element(s) is/are indicated by the upwards arrow i; conversely, when the concentration of any of the elements in the case group is/are lower statistically significantly, the element(s) is/are indicated by the downwards arrow i.

As seen from FIG. 17, the result of P(↑), Ag(↑), Sn(↑) and S(↑) was obtained for the male patients with colon cancer, which means that the concentrations of the 4 elements of P, Ag, Sn, and S in the case group were significantly higher. For the male patients with prostate cancer, the result of P(↓), Ca(↓), Zn(↑), Sn(↑) and S(↓) was obtained. For the female patients with colon cancer, the result of P(↓), Ca(↓), Mn(↑), Rb(↓), and Sn(↑) was obtained. For the female patients with breast cancer, the result of Ca(↑), Ti(↑), Mn(↑), Fe(↑), Zn(↑), and Rb(↓) was obtained. It was understood that the elements in which significant difference was observed were different according to the male or female patients, and were different according to the body part that suffers from cancer also. The risk of having "cancer" was able to be estimated based on the elements in which significant difference was observed between the control group and the case group; however, it was judged that the elements causing significant difference were not suitable for an indicator for knowing the risk of having cancer. This was because the extracted elements were different according to the body part that suffers from cancer and because the ups and downs of the concentration of the extracted elements that affected the discrimination could be opposite according to the body part that suffers from cancer.

Accordingly, using all the concentration data of the 16 elements that had their measurement values for all the subjects (all the serums), analysis was carried out based on pattern recognition. Concretely speaking, an equation capable of best discriminating the difference between the case group and the control group was automatically generated with a computer program (SAS, SPSS and so on) using the data of the 17 items in total including the concentration data of the 16 elements and the age data for the case group and the control group. Even if any of discriminant analysis, multiple regression analysis, and logistic analysis was used, the discriminant function thus derived was expressed as the following equation (4).

Discriminant value (Score) $(D)=F(\text{age, Na, Cl S} \ldots, \text{Ti, Rb})$ (4)

The risk of having cancer can be estimated which of the case group and the control group the discriminant value (D) belongs to. The analysis result in the case where discriminant analysis was used is shown in FIGS. 18 and 19.

As shown in FIG. 18, in the case of the male patients with prostate cancer, the 30 subjects were included in the control group and the 18 subjects were included in the case group; when discrimination was conducted using the equation (4), 30 out of the 30 subjects in the control group were judged "belonging to the control group" (the specificity was 100%), and 16 out of the 18 subjects in the case group were judged "belonging to the case group" (the sensitivity was 88.9%). In the case of the male patients with colon cancer, 26 out of the 30 subjects in the control group (the specificity was 86.7%) and 39 out of the 43 subjects in the case group (the sensitivity was 90.7%) were judged accurately. Moreover, as shown in FIG. 19, in the case of the female patients with colon cancer, 29 out of the 30 subjects in the control group (the specificity was 96.7%) and 18 out of the 20 subjects in the case group (the sensitivity was 90%) were judged correctly. In the case of the female patients with breast cancer, 30 out of the 30 subjects in the control group (the specificity was 100%) and 28 out of the 30 subjects in the case group (the sensitivity was 93.3%) were judged correctly.

Figure 20:
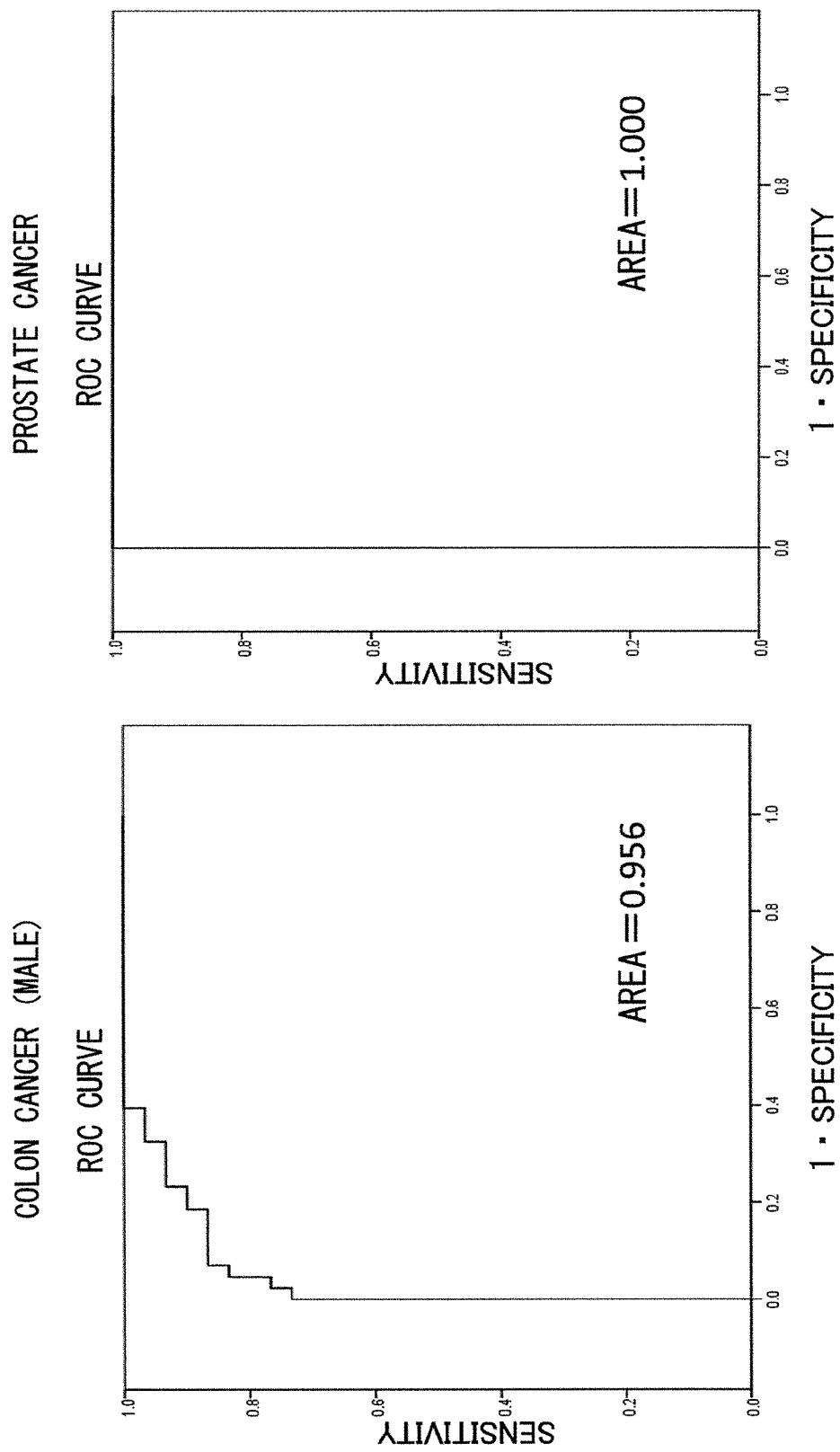
FIG. 20 is a table showing the result of ROC analysis of the prostate cancer patients (male) and the colon cancer patients (male) which are obtained in the modification (development) of the cancer evaluation method according to the present invention.
Figure 21:
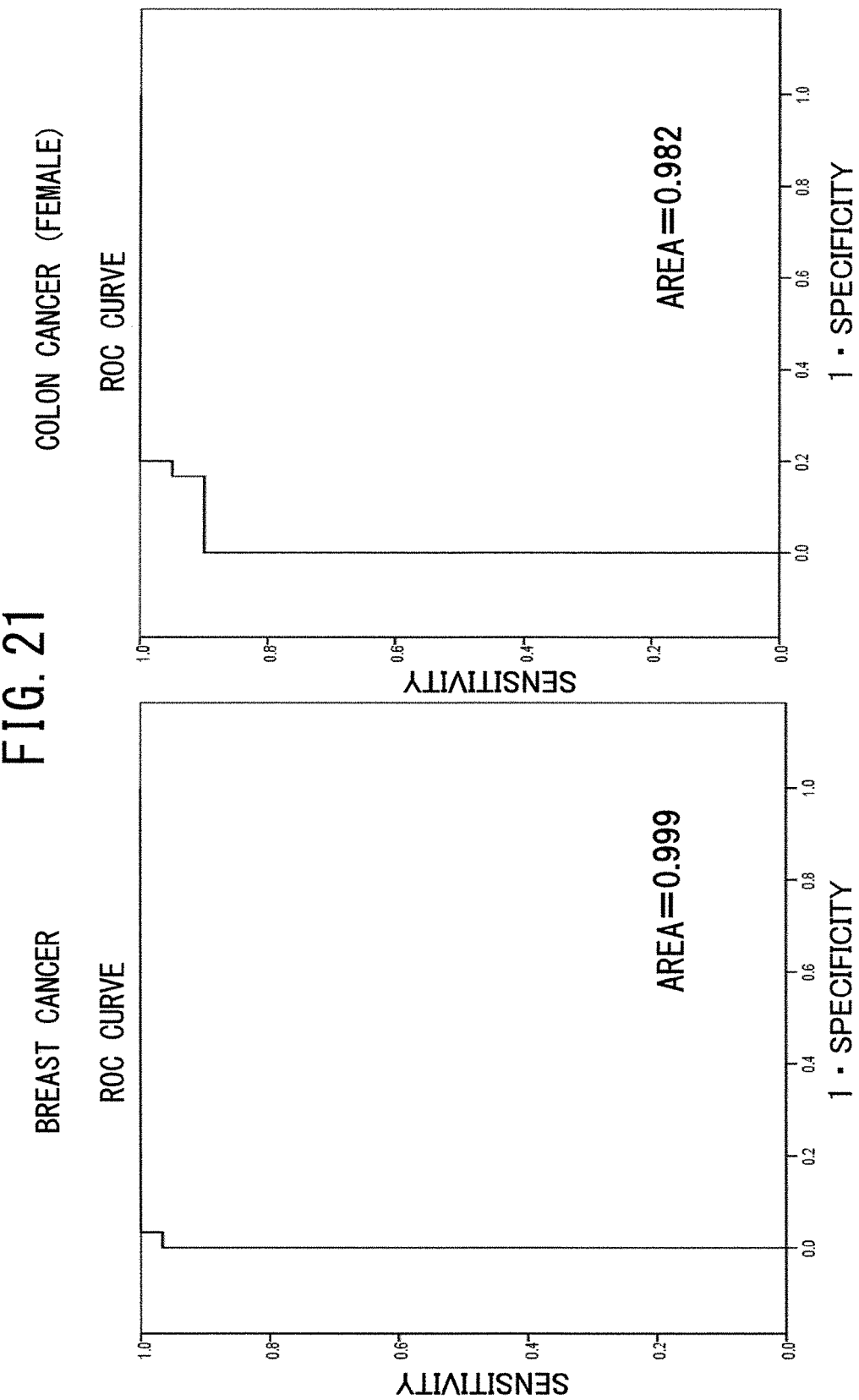
FIG. 21 is a table showing the result of ROC analysis of the colon cancer patients (female) and the breast cancer patients (female) which are obtained in the modification (development) of the cancer evaluation method according to the present invention.

Subsequently, ROC analysis was carried out as a method of confirming the reliability of the result which was produced by the discriminant introduced. With the ROC analysis used here, while successively changing the discriminant value (score) (D) that was calculated from the equation (4) from the lowest value to the highest value, the sensitivity and the specificity were calculated from the number of the subjects which were separated into the control group and that separated into the case group, thereby generating the figures shown in FIGS. 20 and 21. The vertical axis represents the sensitivity and the horizontal axis represents the (1—Specificity) in these two figures. The goodness of fit of the discriminant (prediction) can be judged according to the magnitude of the lower area that is partitioned by the curve in these figures. The lowest value of the area is set as 0 and the highest value thereof is set as 1, which means that if the magnitude of the area is closer to 1, the discriminant is more accurate. As shown in FIG. 20, the area is 0.956 in the case of the male patients with colon cancer, and the area is 1.000 in the case of the male patients with prostate cancer. As shown in FIG. 21, the area is 0.999 in the case of the female patients with breast cancer, and the area is 0.982 in the case of the male patients with colon cancer. It is found that sufficiently high values are obtained in any of these cases. Since it was reported that the ROC areas of the existing screening methods for diagnosing cancer such as fecal occult blood reaction for colon cancer and mammography for breast cancer were 0.7 to 0.8, it will be understood that the method of the present invention is better than these two screening methods.

The discriminant function calculated by the discriminant analysis is expressed, for example, in the case of prostate cancer, in the following equation (5) (see the left side of FIG. 22).

$D=0.0903949 \times \text{Age} + 0.0000053 \times \text{Na} - 0.0002593 \times \text{Mg} + 0.0000492 \times \text{Al} - 0.0000252 \times \text{P} + 0.0000105 \times \text{K} + 0.000046 \times \text{Ca} + 0.0006909 \times \text{Ti} + 0.0154933 \times \text{Mn} - 0.0001292 \times \text{Fe} - 0.0027147 \times \text{Cu} - 0.0002606 \times \text{Zn} + 0.0166826 \times \text{Se} - 0.0077824 \times \text{Rb} - 0.0019460 \times \text{Ag} + 0.0193273 \times \text{Sn} - 0.0000003 \times \text{S} - 21.5837825$ (Constant) (5)

In the case of the male patients with colon cancer, the discriminant function is expressed as shown in the right side of FIG. 22. Moreover, in the case of the female patients with breast cancer, the discriminant function is expressed as shown in the left side of FIG. 23, and in the case of the female patients with colon cancer, the discriminant function is expressed as shown in the right side of FIG. 23.

By inputting the age data and the concentration data of the 16 elements into these discriminants, the value (discriminant score) of the discriminant functions can be obtained. The discriminant score and the probability (probability of normality and probability of cancer) that the subjects or patients are divided (grouped) into the control group or the case group in the case of the male patients with colon cancer are shown in FIG. 24. For example, if the age data and the concentration data of the 16 elements of one of the patients are inputted into a corresponding one of the discriminants to result and the discriminant sore of 1.77860 is obtained, it is found by calculation that the probability of non-cancer and the probability of cancer are 0.438% and 99.562%, respectively. Thus, it can be estimated that this patient has a very high possibility of having colon cancer.

The discriminant score, the probability of normality, and the probability of having cancer in the case of the male patients with colon cancer are shown in FIG. 25. Moreover, the discriminant score, the probability of normality, and the probability of cancer in the cases of the female patients with breast cancer and the female patients with colon cancer are shown in FIGS. 26 and 27, respectively. In the same way as the case of the male patients with colon cancer, the probability (probability of normality and probability of cancer) that the patients are divided into the control group or the case group can be found from these figures; therefore, the possibility that these patients have any one of these types of cancer can be estimated with high accuracy. In other words, since different discriminants are used according to the type (body part) of cancer, not only the possibility of having cancer can be found but also the type (body part) of possible cancer can be identified.

Figure 28:
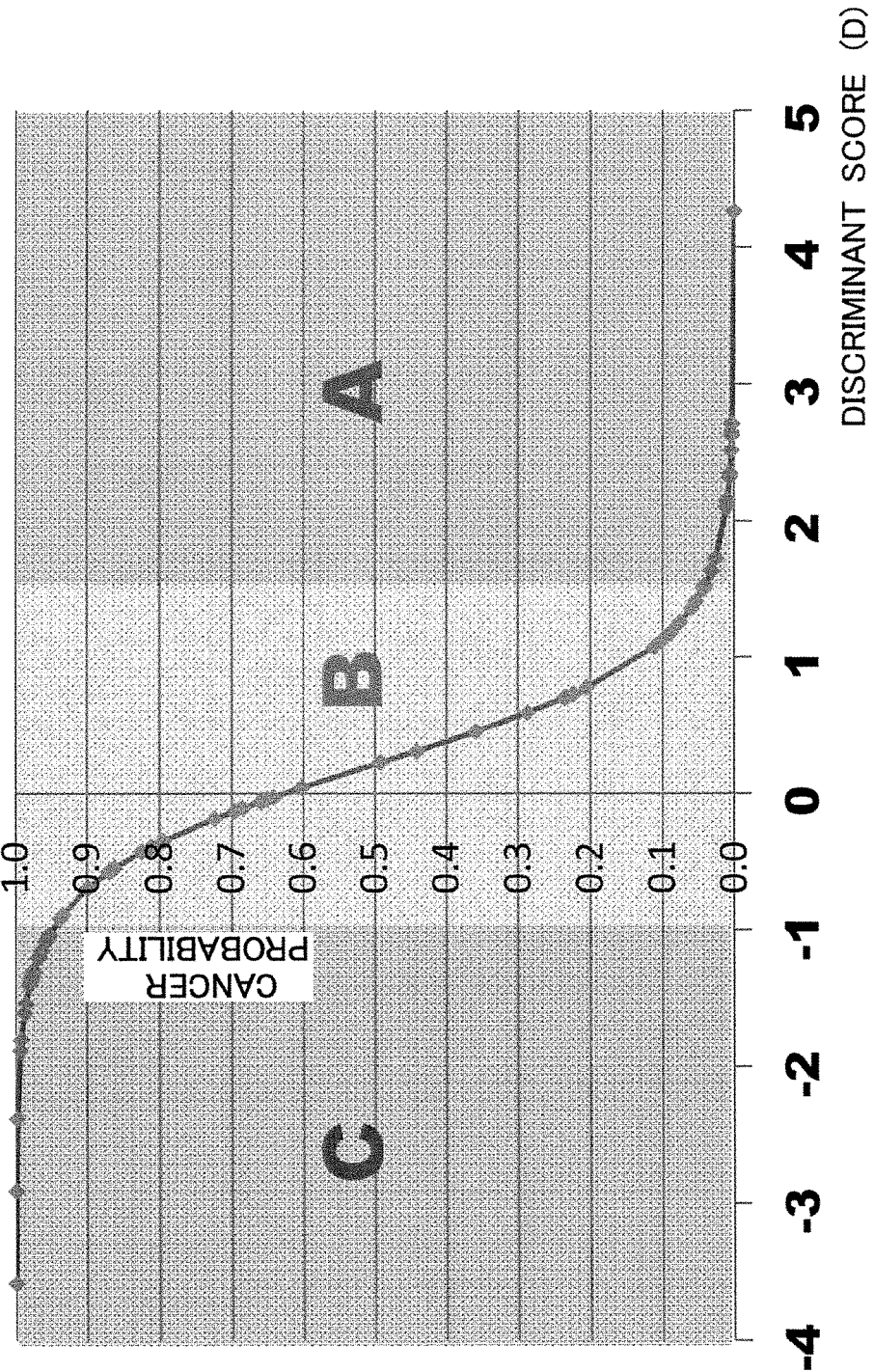
FIG. 28 is a graph showing the discriminant score and the discriminant probability of the colon cancer patients (male) which are used in the modification (development) of the cancer evaluation method according to the present invention.
Figure 29:
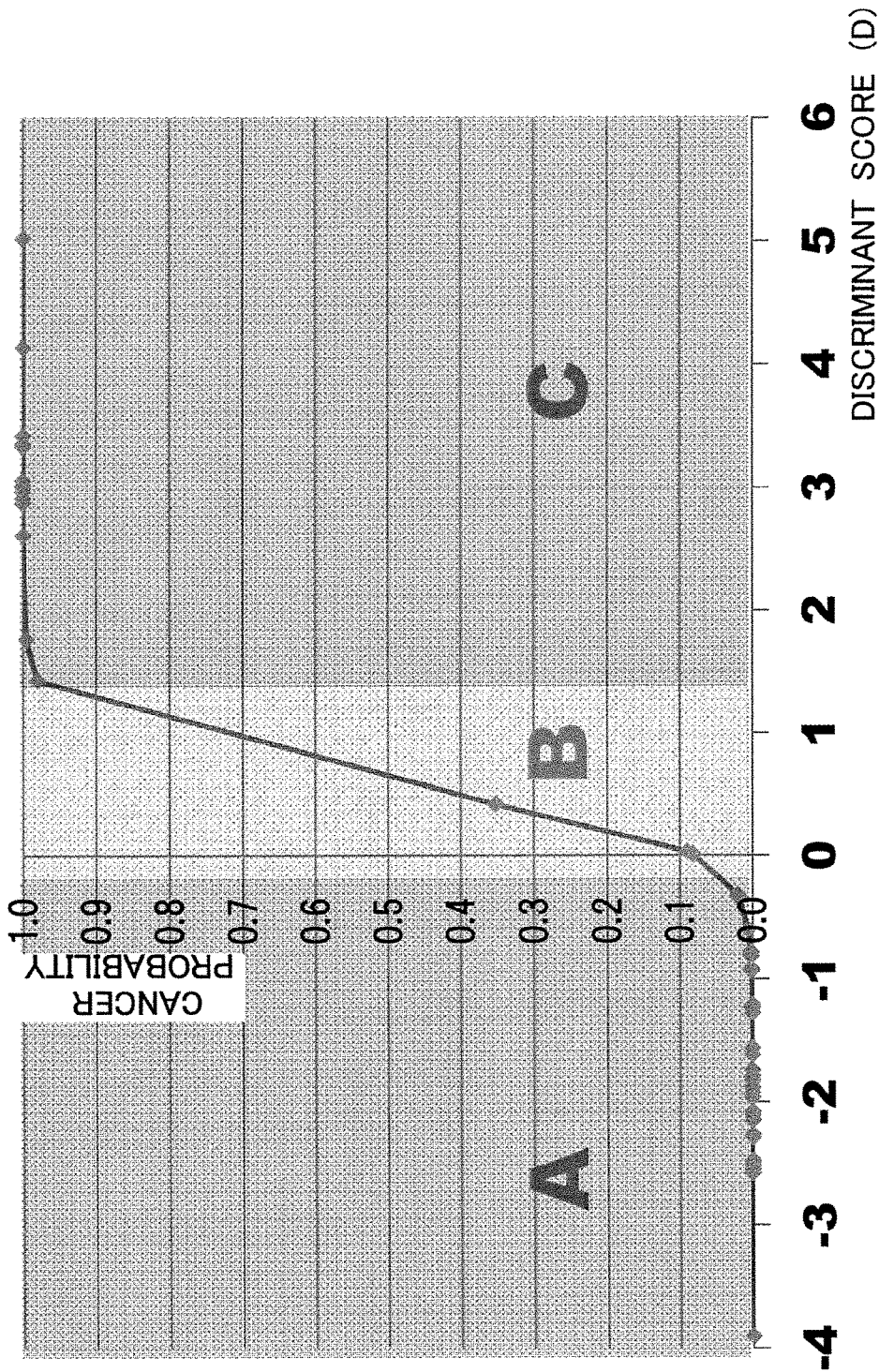
FIG. 29 is a graph showing the discriminant score and the discriminant probability of the prostate cancer patients (male) which are used in the modification (development) of the cancer evaluation method according to the present invention.
Figure 30:
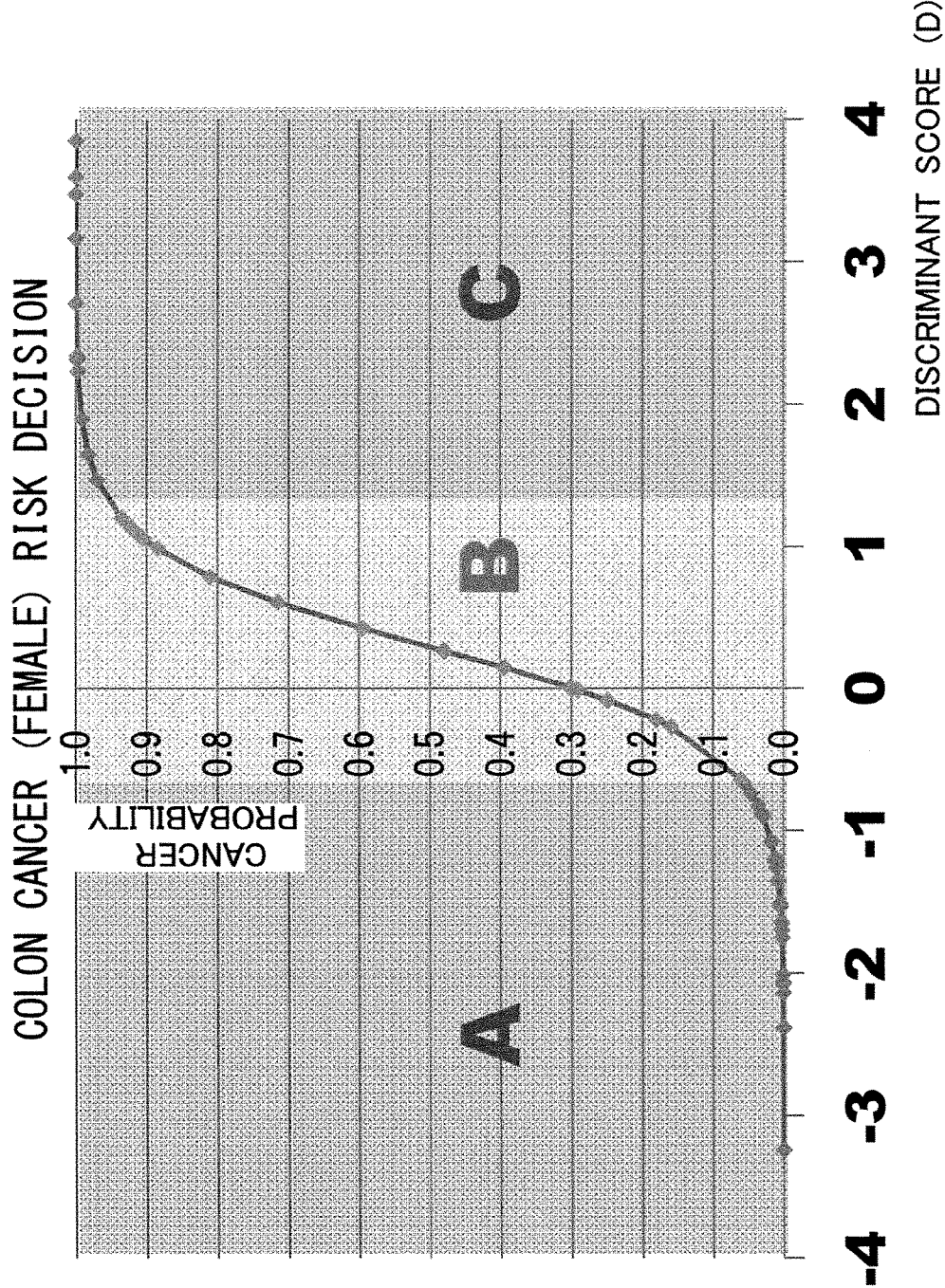
FIG. 30 is a graph showing the discriminant score and the discriminant probability of the breast cancer patients (female) which are used in the modification (development) of the cancer evaluation method according to the present invention.
Figure 31:
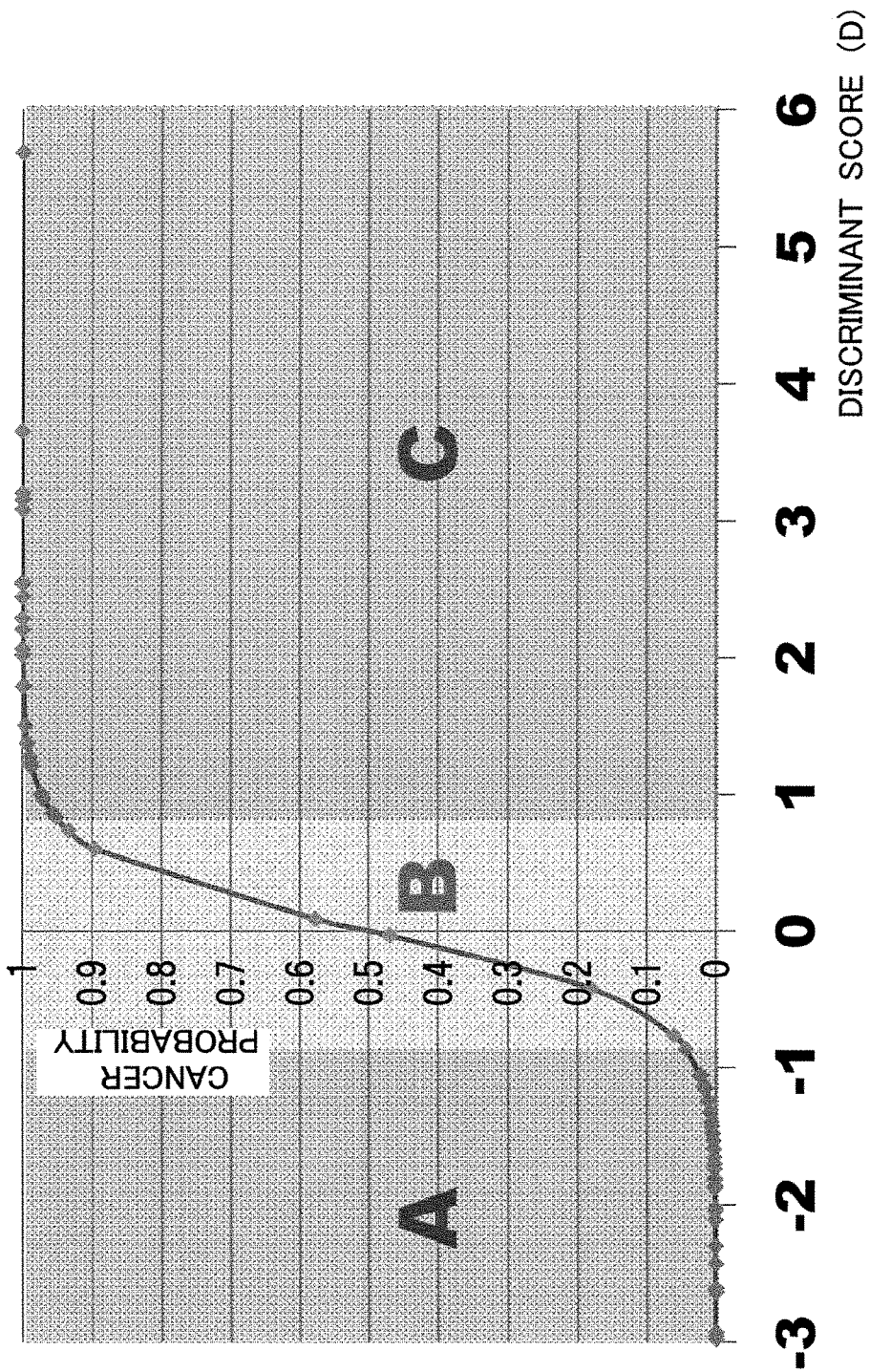
FIG. 31 is a graph showing the discriminant score and the discriminant probability of the colon cancer patients (female) which are used in the modification (development) of the cancer evaluation method according to the present invention.

FIGS. 28 to 31 show the graphs formed to visually facilitate understanding using the data which are calculated from the discriminant functions and shown in FIGS. 24 to 27. The horizontal axis represents the discriminant score (D) and the vertical axis represents the probability of cancer. For example, in the case of the male patients with prostate cancer shown in FIG. 29, the probability of cancer is 95% or higher if D is 1.4 or more; if so, "Judgement C" is given to the subject in question, which means that he/she is judged to have a highest risk of this cancer. If D is 0.3 or less, the probability of cancer is equal to 5% or lower and therefore, "Judgement A" is given to the subject in question, which means that he/she is judged to have a low risk of this cancer. If D is in the range from 0.3 to 1.4, the probability of cancer is in the range from 5% to 95% and therefore, "Judgement B" is given to the subject in question, which means that he/she is judged to be necessary to receive follow-up observation. In the cases of FIG. 28 and FIGS. 30 and 31 also, judgement of the risk of having cancer can be made similarly.

As explained above, it was confirmed that the risk of having cancer (and the body part suffering from cancer) can be estimated with high accuracy by analyzing the pattern (concentration balance) based on the age data and the concentration data of the 16 elements.

In Example 3, similar to the aforementioned Examples 1 and 2, a method of diagnosing the risk of having cancer is realized utilizing the fact that the concentration balances (concentration distribution patterns) caused by the ups and downs of the in-serum concentrations of the elements (the set of evaluation elements) are clearly different from each other between the case group and the control group, instead of paying attention to the change of the in-serum concentrations of the specific elements. Therefore, this method is a new one which is different from the conventional methods.

In Example 3, discriminant functions were calculated for the male patients with colon cancer, the male patients with prostate cancer, the female patients with colon cancer, and the female patients with breast cancer; however, it is anticipated that similar results will be obtained for any other type (body part) of cancer. The fact that the risk of having cancer can be estimated for different types (body parts) of cancers in Example 3 with a single blood sampling destroys the conventional wisdom about the existing cancer diagnosis methods, which provides a new method.

In addition, in Example 3, all of the 16 elements having their concentration data for the subjects or serums in the control group and those in the case group were used as the set of evaluation elements and therefore, Mahalanobis' generalized distance has only one value. In Example 3, it was confirmed that the discriminants generated under such the condition as described here also were effective similar to aforementioned Examples 1 and 2. If any part of the 16 elements having their concentration data for the subjects or serums in the control and case groups are chosen and used as the set of evaluation elements (the combination of the elements is changed), Mahalanobis' generalized distance will have plural values. In this case, as already explained in the basic principle of the cancer evaluation method of the present invention, it is preferred that a combination of the elements is chosen such that Mahalanobis' generalized distance is maximized in value.

Example 4

This Example also corresponds to the modification/development of the cancer evaluation method of the present invention shown in FIG. 14 similar to aforementioned Example 3.

Using only the concentration data of the 16 elements (Na, Mg, Al, P, K, Ca, Ti, Mn, Fe, Zn, Cu, Se, Rb, Ag, Sn, S) that were measured in aforementioned Example 3 as the analyzing data, discrimination was carried out in the same way as that of aforementioned Example 3 except that the age data of the subjects were not used. As a result, a similar discrimination result to that of Example 3 was obtained. In Example 4, as seen from this discrimination result, the effect on the discrimination by the non-use of the age data of the subjects was not observed. However, the onset of cancer has a relationship with the age; therefore, it is anticipated that discrimination including the age data is preferred from the viewpoint of raising the accuracy of the discrimination result.

INDUSTRIAL APPLICABILITY

The present invention is widely applicable to the fields where quick and convenient estimation of the presence or absence of suffering cancer of humans (or animals) is expected.

DESCRIPTION OF REFERENCE NUMERALS 1 test tube
2 serum sample
5, 5A in-serum element concentration measurement section
10, 10A cancer evaluation system
11, 11A data storage section
12, 12A discriminant function generation section
13, 13A evaluation result operation section

The invention claimed is:
1. A cancer evaluation method, comprising:
(a) preparing first to fourth discriminant functions dedicated respectively to male colon cancer, male prostate cancer, female colon cancer, and female breast cancer using a discriminant function generation program based on a correlation among concentrations of a set of evaluation chemical elements contained in serums of subjects who belong to a case group and concentrations of the set of evaluation chemical elements contained in serums of subjects who belong to a control group with respect to male colon cancer, male prostate cancer, female colon cancer, and female breast cancer;

wherein each of the first to fourth discriminant functions includes concentrations of the set of evaluation chemical elements as its explanatory variables, and the set of evaluation chemical elements is a combination of 16 chemical elements selected from the group consisting of Na, Mg, Al, P, K, Ca, Ti, Mn, Fe, Zn, Cu, Se, Rb, Ag, Sn and S;

(b) preparing a first relationship between a discriminant value of the first discriminant function and a probability of belonging to the case group of male colon cancer, a second relationship between a discriminant value of the second discriminant function and a probability of belonging to the case group of male prostate cancer, a third relationship between a discriminant value of the third discriminant function and a probability of belonging to the case group of female colon cancer, and a fourth relationship between a discriminant value of the fourth discriminant function and a probability of belonging to the case group of female breast cancer;

(c) obtaining concentration data of the set of evaluation chemical elements contained in a serum of a target subject;

(d) calculating first to fourth discriminant values of the target subject by applying the concentration data of the set of evaluation chemical elements of the target subject to the first to fourth discriminant functions using a computer; and (e) comparing respectively the first to fourth discriminant values of the target subject with the first to fourth relationships, thereby evaluating a risk of male colon cancer, male prostate cancer, female colon cancer, and female breast cancer of the target subject using the computer;

wherein whether or not the target subject is judged to have a high risk of male colon cancer based on a result of comparing a probability that the target subject belongs to the case group of male colon cancer with a first reference value of the first relationship;

whether or not the target subject is judged to have a high risk of male prostate cancer based on a result of comparing a probability that the target subject belongs to the case group of male prostate cancer with a second reference value of the second relationship;

whether or not the target subject is judged to have a high risk of female colon cancer based on a result of comparing a probability that the target subject belongs to the case group of female colon cancer with a third reference value of the third relationship; and whether or not the target subject is judged to have a high risk of female breast cancer based on a result of comparing a probability that the target subject belongs to the case group of female breast cancer with a fourth reference value of the fourth relationship.

2. The cancer evaluation method according to claim 1, wherein each of the first to fourth discriminant functions includes an age as its explanatory variable; and age data of the target subject is applied to the first to fourth discriminant functions in addition to the first to fourth discriminant values of the target subject.

3. A cancer evaluation system comprising:

(a) a data storage device that is configured to store concentration data of a set of evaluation chemical elements contained in a serum of a target subject;

wherein the set of evaluation chemical elements is a combination of 16 chemical elements selected from the group consisting of Na, Mg, Al, P, K, Ca, Ti, Mn, Fe, Zn, Cu, Se, Rb, Ag, Sn and S;

(b) a discriminant function generation program that is configured to generate first to fourth discriminant functions dedicated respectively to male colon cancer, male prostate cancer, female colon cancer, and female breast cancer based on a correlation among concentrations of a set of evaluation chemical elements contained in serums of subjects who belong to a case group and concentrations of the set of evaluation chemical elements contained in serums of subjects who belong to a control group with respect to male colon cancer, male prostate cancer, female colon cancer, and female breast cancer;

wherein each of the first to fourth discriminant functions includes concentrations of the set of evaluation chemical elements as its explanatory variables; and (c) an evaluation result controller that is configured to calculate first to fourth discriminant values of the target subject by applying the concentration data of the set of evaluation chemical elements of target subject stored in the data storage device to the first to fourth discriminant functions generated by the discriminant function generation program, wherein the first to fourth discriminant values of the target subject are respectively compared with the first to fourth relationships, thereby evaluating a risk of male colon cancer, male prostate cancer, female colon cancer, and female breast cancer of the target subject;

wherein whether or not the target subject is judged to have a high risk of male colon cancer based on a result of comparing a probability that the target subject belongs to the case group of male colon cancer with a first reference value of the first relationship;

whether or not the target subject is judged to have a high risk of male prostate cancer based on a result of comparing a probability that the target subject belongs to the case group of male prostate cancer with a second reference value of the second relationship;

whether or not the target subject is judged to have a high risk of female colon cancer based on a result of comparing a probability that the target subject belongs to the case group of female colon cancer with a third reference value of the third relationship; and whether or not the target subject is judged to have a high risk of female breast cancer based on a result of comparing a probability that the target subject belongs to the case group of female breast cancer with a fourth reference value of the fourth relationship.

4. The cancer evaluation system according to claim 3, wherein in the evaluation result controller, each of the first to fourth discriminant functions includes an age as its explanatory variable; and age data of the target subject is applied to the first to fourth discriminant functions in addition to the concentration data of the set of evaluation chemical elements of the target subject.

5. The cancer evaluation method according to claim 1, wherein the concentration data of the set of evaluation chemical elements of the target subject is measured using any one of Inductively-Coupled Plasma Optical Emission Spectroscopy (ICP-OES), Inductively-Coupled Plasma Mass Spectroscopy (ICP-MS), Atomic Absorption Spectrometry (AAS), and X-Ray Fluorescence analysis (XRF).

6. The cancer evaluation method according to claim 1, wherein the probability that the target subject belongs to the case group of each of male colon cancer, male prostate cancer, female colon cancer, and female breast cancer is calculated using a following equation:

$$\text{Probability}=1/[1+\exp(-\text{Calculated Discriminant Value})].$$

7. The cancer evaluation method according to claim 1, wherein when the calculated probability that the target subject belongs to the case group of one of male colon cancer, male prostate cancer, female colon cancer, and female breast cancer is equal to or greater than a relatively high reference value, the target subject is judged to have a high risk of the one of male colon cancer, male prostate cancer, female colon cancer, and female breast cancer;
when the calculated probability that the target subject belongs to the case group of the one of male colon cancer, male prostate cancer, female colon cancer, and female breast cancer is equal to or less than a relatively low reference value, the target subject is judged to have a low risk of the one of male colon cancer, male prostate cancer, female colon cancer, and female breast cancer; and
when the calculated probability that the target subject belongs to the case group of the one of male colon cancer, male prostate cancer, female colon cancer, and female breast cancer is in a range from the relatively high reference value to the relatively low reference value, the target subject is judged to be necessary to receive follow-up observation with respect to the one of male colon cancer, male prostate cancer, female colon cancer, and female breast cancer.

8. The cancer evaluation method according to claim 1, wherein when the calculated probability that the target subject belongs to the case group of each of male colon cancer, male prostate cancer, female colon cancer, and female breast cancer is equal to or less than a predetermined reference value, the target subject is judged to have a low risk of all of male colon cancer, male prostate cancer, female colon cancer, and female breast cancer.

9. The cancer evaluation system according to claim 3, wherein the concentration data of the set of evaluation chemical elements of the target subject is measured using any one of Inductively-Coupled Plasma Optical Emission Spectroscopy (ICP-OES), Inductively-Coupled Plasma Mass Spectroscopy (ICP-MS), Atomic Absorption Spectrometry (AAS), and X-Ray Fluorescence analysis (XRF).

10. The cancer evaluation system according to claim 3, wherein the probability that the target subject belongs to the case group of each of male colon cancer, male prostate cancer, female colon cancer, and female breast cancer is calculated using a following equation:

$$\text{Probability}=1/[1+\exp(-\text{Calculated discriminant value})].$$

11. The cancer evaluation system according to claim 3, wherein when the calculated probability that the target subject belongs to the case group of one of male colon cancer, male prostate cancer, female colon cancer, and female breast cancer is equal to or greater than a relatively high reference value, the target subject is judged to have a high risk of the one of male colon cancer, male prostate cancer, female colon cancer, and female breast cancer;
when the calculated probability that the target subject belongs to the case group of the one of male colon cancer, male prostate cancer, female colon cancer, and female breast cancer is equal to or less than a relatively low reference value, the target subject is judged to have a low risk of male colon cancer, male prostate cancer, female colon cancer, and female breast cancer; and
when the calculated probability that the target subject belongs to the case group of the one of male colon cancer, male prostate cancer, female colon cancer, and female breast cancer is in a range from the relatively high reference value to the relatively low reference value, the target subject is judged to be necessary to receive follow-up observation with respect to the one of male colon cancer, male prostate cancer, female colon cancer, and female breast cancer.

12. The cancer evaluation system according to claim 3, wherein when the calculated probability that the target subject belongs to the case group of each of male colon cancer, male prostate cancer, female colon cancer, and female breast cancer is equal to or less than a predetermined reference value, the target subject is judged to have a low risk of all of male colon cancer, male prostate cancer, female colon cancer, and female breast cancer.

\* \* \* \* \*